US011918352B2

(12) United States Patent
MacIntyre

(10) Patent No.: US 11,918,352 B2
(45) Date of Patent: Mar. 5, 2024

(54) NON-INVASIVE DETERMINATION OF A PHYSIOLOGICAL STATE OF INTEREST IN A SUBJECT

(71) Applicant: ISBRG CORP., Mississauga (CA)

(72) Inventor: Duncan James MacIntyre, Mississauga (CA)

(73) Assignee: ISBRG CORP., Mississauga (CA)

( * ) Notice: Subject to any disclaimer, the term of this patent is extended or adjusted under 35 U.S.C. 154(b) by 41 days.

(21) Appl. No.: 16/410,587

(22) Filed: May 13, 2019

(65) Prior Publication Data

US 2022/0211299 A1     Jul. 7, 2022

Related U.S. Application Data

(60) Provisional application No. 62/671,877, filed on May 15, 2018.

(51) Int. Cl.
*A61B 5/1455*     (2006.01)
*A61B 5/00*     (2006.01)
*A61B 5/145*     (2006.01)

(52) U.S. Cl.
CPC .......... *A61B 5/1455* (2013.01); *A61B 5/4845* (2013.01); *A61B 5/7264* (2013.01); *A61B 5/14532* (2013.01); *A61B 5/14546* (2013.01)

(58) Field of Classification Search
CPC ... A61B 5/1455; A61B 5/4845; A61B 5/7264; A61B 5/14532; A61B 5/14546;
(Continued)

(56) References Cited

U.S. PATENT DOCUMENTS 5,361,758 A    11/1994   Hall et al.
5,429,128 A    7/1995   Cadell et al.
(Continued)

FOREIGN PATENT DOCUMENTS

CA          2895969        7/2014
WO    WO 93/16629 A1   9/1993

OTHER PUBLICATIONS

Fletcher, Lauren, et al. "Feasibility of an implanted, closed-loop, blood-glucose control device." Immunology 230. (Year: 2001).*

(Continued)

*Primary Examiner* — Chu Chuan Liu
(74) *Attorney, Agent, or Firm* — Michele V. Frank; Venable LLP

(57) ABSTRACT

A method for non-invasively determining a physiological state of interest in a subject is described. The method involves, placing a body part in contact with a receptor, and directing a source of electromagnetic radiation (EMR) over a range of wavelengths onto body part so that the EMR reaches the blood and interstitial fluid within the body part. The EMR that is absorbed by, reflected by, or transmitted through, the blood and interstitial fluid of the body part is measured, and a spectrum over the range of wavelengths obtained. The spectrum is analyzed to determine an amount of two or more than two analytes within the blood and interstitial fluid of the body part and a biochemical profile is derived. The biochemical profile is used to determine the physiological state of interest in the subject. The physiological state of interest in the subject may be selected from the group of intoxication arising from cannabis, alcohol, a combination of cannabis and alcohol, opiates, fentanyl, amphetamines, phencyclidine, sedatives, anxyolytics, cocaine, caffeine, and nicotine consumption.

20 Claims, 5 Drawing Sheets

(58) Field of Classification Search
CPC . A61B 5/14551; A61B 5/1451; A61B 5/6826; A61B 5/0075
USPC .......................................................... 600/310
See application file for complete search history.

(56) References Cited

U.S. PATENT DOCUMENTS

| | | | |
|---|---|---|---|
| 6,040,578 A | 3/2000 | Malin et al. | |
| 6,236,047 B1 | 5/2001 | Malin et al. | |
| 6,240,306 B1 | 5/2001 | Rohrscheib et al. | |
| 6,657,717 B2 | 12/2003 | Cadell et al. | |
| 6,741,876 B1 | 5/2004 | Scecina et al. | |
| 6,961,599 B2* | 11/2005 | Lambert | A61B 5/14532 600/318 |
| 2006/0173256 A1* | 8/2006 | Ridder | G01N 21/274 600/316 |
| 2010/0269566 A1* | 10/2010 | Carroll | A61B 5/14517 73/23.3 |
| 2013/0248695 A1 | 9/2013 | Macintyre et al. | |
| 2015/0110721 A1* | 4/2015 | Conrad | A61B 5/0071 424/9.34 |
| 2020/0268252 A1 | 8/2020 | Litvinova | |

OTHER PUBLICATIONS

Anderson, et al., Sex Differences in the Effects of Marijuana on Simulated Driving Performance. 2010, J Psychoactive Drugs, 42(1), 19-30. doi:10.1080/02791072.2010.10399782.

Hartman et al., "Cannabis Effects on Driving Lateral Control with and Without Alcohol", Drug Alcohol Depend., 154, 25-37. doi:10.1016/j.drugalcdep.2015.06.015.

Haslacher et al., "A Combination of Routine Blood Analytes predicts Fitness Decrement in Elderly Endurance Athletes", PLOS ONE, 12(5): pp. 1-14, May 5, 2017.

Lenné et al., "The Effects of Cannabis and Alcohol on Simulated Arterial Driving: Influences of Driving Experience and Task Demand", Accident Analysis and Prevention, 42(3), 859-866, 2010. doi:10.1016/j.aap.2009.04.021.

Marsot et al., "Comparison of Cannabinoid Concentrations in Plasma, Oral Fluid and Urine in Occasional Cannabis Smokers After Smoking Cannabis Cigarette", J Pharm Pharm Sci, 19: 411-422, 2016.

Mirowski et al., Comparing SVM and Convolutional Networks for Epileptic Seizure Prediction from Intracranial EEG, published IEEE Workshop on Machine Learning for Signal Processing, pp. 244-249, 2008.

Newmeyer et al., "Cannabis Edibles Blood and Oral Fluid Cannabinoid Pharmacokinetics and Evalution of Oral Fluid Screening Devices for Predicting $\Delta^9$—Tetrahydrocannabinol in Blood and Oral Fluid Following Cannabis Brownie Administration", Clinical Chemistry vol. 63, Issue 3, pp. 647-662, 2017.

Ronen et al., "Effects of THC on Driving Performance, Physiological State and Subjective Feelings Relative to Alcohol", Accident Analysis and Prevention, 40(3), 926-934, 2008. doi:10.1016/j.aap.2007.10.011.

Ronen et al., "The Effect of Alcohol, THC and Their Combination on Perceived Effects, Willingness to Drive and Performance of Driving and Non-Driving Tasks", Accident Analysis and Prevention, 42(6), 1855-1865, 2010.

Schwope et al., "Direct Quantification of Cannabinoids and Cannabinoid Glucuronides in Whole Blood by Liquid Chromatography Tandem Mass Spectrometry", Anal Bioanal Chem. 410:1273-1283, Sep. 2011.

Skopp et al., "An Investigation of the Stability of Free and Glucuronidated 11-Nor-$\Delta^9$-Tetrahydrocannabinol-9-carboxylic Acid in Authentic Urine Samples", Journal of Analytical Toxicology, 28: 35-40, 2004.

International Search Report and Written Opinion for International Patent Application No. PCT/CA2022/050208, dated May 16, 2022, 5 pages.

* cited by examiner

NON-INVASIVE DETERMINATION OF A PHYSIOLOGICAL STATE OF INTEREST IN A SUBJECT

RELATED APPLICATIONS

This application claims the benefit of U.S. Provisional Patent Application Ser. No. 62/671,877, filed May 15, 2018, the entire disclosure of which is hereby incorporated herein by reference in its entirety.

FIELD OF INVENTION

The present invention relates to non-invasive methods and a device for determining a physiological state of interest in a subject. The methods are used to determining biochemical profile or fingerprint, that is indicative of the physiological state of interest in the subject.

BACKGROUND OF THE INVENTION

The physiological state of a subject may be established by measuring a range of metabolic parameters using a variety of measurement tools. For example, Haslacher H., et. al., (2017, PLoS ONE 12(5): e0177174. doi.org/10.1371/journal. pone.0177174) teach the measurement of 12 blood constituents to predict physical capability of an elderly subject. However, a sample of blood is required for the analysis and the various blood constituents are measured using a range of techniques, including photometric, enzymatic, enzymatic colourimetry, ELISA, and others.

The quantification of cannabinoids in whole blood using liquid chromatography and tandem mass spectrometry is described in Schwope D., et. al. (2011, Anal. Bioanal Chem. 410:1273-1283), and in whole blood and urine using GC-MS, is disclosed in Marsot, A. et. al. (2016, J. Pharm. Pharm Sci 19:411-422). With these methods the analysis is performed on a sample of blood obtained from the subject.

Non-invasive measurement of the concentration of a compound or analyte in the fluid or tissue of part of a subject, such as the finger, arm or earlobe, may be used to determine the presence or absence of the compound within the fluid or tissue. These methods involve measuring the absorption spectra of the body part and comparing this absorption spectrum against a control absorption spectrum obtained for the compound of interest and determining if the compound of interest is present in the sampled body part.

For example, U.S. Pat. No. 5,361,758 (Hall et al.) describes a non-invasive method to measure the blood glucose concentration in diabetic patients. The method involves measuring the concentration of constituents of blood using light in the near-infrared range. A similar method is described in U.S. Pat. No. 6,741,876 (Seciena et al.). In U.S. Pat. Nos. 6,236,047 and 6,040,578, Malin et al. describe a method for determining the concentration of a blood compound using light in the near infrared range by analyzing diffusively reflecting radiation emerging from the irradiated sample. U.S. Pat. No. 5,429,128 discloses a finger receptor for repeatable non-invasive measurement of blood analytes using near infrared radiation.

While using LC-TMS or GC-MS may accurately determine the concentration delta-9-tetrahydrocannabinol (THC; the psychoactive component associated with cannabinoid intoxication), or 11-nor-9-carboxy-THC (THC-COOH, an inactive metabolite), within a sample of whole blood, THC fat soluble and it is known to clear the blood quickly, yet persist within fatty tissues of the body for a period of time. Furthermore, as the fat tissues are metabolized, the THC is redistributed slowly back into the bloodstream. As a result, THC or THC-COOH are not a reliable markers of cannabis intoxication.

SUMMARY OF THE INVENTION

The present invention relates to non-invasive methods and a device for determining a physiological state of interest in a subject. The methods are used to determining biochemical profile or fingerprint, that is indicative of the physiological state of interest in the subject According to the present invention there is provided a non-invasive method (A) of non-invasively determining a physiological state of interest in a subject comprising,
  (a) placing a body part in contact with a receptor
  (b) directing a source of electromagnetic radiation (EMR) over a range of wavelengths through the receptor and onto body part so that the EMR reaches the blood and interstitial fluid within the body part;
  (c) measuring the EMR absorbed by, reflected by, or transmitted through, the blood and interstitial fluid of the body part with a detector to obtain a spectrum over the range of wavelengths;
  (d) performing a quantitative mathematical analysis of the spectrum using an algorithm to determine an amount of two or more than two analytes within the blood and interstitial fluid of the body part; and
  (e) comparing the amount of the two or more than two analytes against a reference value of the two or more analytes to derive a biochemical profile, the biochemical profile used to determine the physiological state of interest in the subject.

In the method (A) described above, in the step of directing, the source of EMR is provided over a range of wavelengths from about 400 to about 2500 nm. The method may include a step of determining a behavioral parameter. Furthermore, the physiological state of interest in the subject may be selected from the group of intoxication, dehydration, hyperglycemia, hypoglycemia, high cholesterol. For example, if the physiological state of interest is:
  i) cannabis induced intoxication, then two or more than two analytes may include: delta-9-tetrahydrocannabinol (THC), THC glucuronide (THCGlu), 11-nor-9-carboxy-THC (THC-COOH), 11-hydroxy THC (11-OH-THC), THC-COOH/11-OH-THC ratio, 11-nor-9-carboxy-THC glucuronide (THC-COOGlu), cannabidol (CBD), cannbinol (CBN), cannabigerol (CBG), delta-9-tetrahydrocannabivarin (THCV), THCV-carboxylic acid, 11-nor-9-carboxy-delta-tetrahydrocannabivarin (THCV-COOH), albumin, apolipoproteins A1 and B (apoA1 and apoB), total protein, bilirubin, prolactin, triglycerides, creatinine, cortisol, glucose, lactate, Total 4, uric acid, blood urea nitrogen (BUN), blood sugar, calcium, ionized calcium, magnesium, sodium, phosphate, and GABA;
  ii) alcohol induced intoxication, then two or more than two analytes may include: alcohol, aldehyde, and lactic acid; or
  iii) intoxication generally, for example arising from a combination of cannabis and alcohol, or from opiates, fentanyl, amphetamines, phencyclidine, sedatives, anxyolytics, cocaine, caffeine, and nicotine consumption, then two or more than two analytes may include: delta-9-tetrahydrocannabinol (THC), THC glucuronide (THCGlu), 11-nor-9-carboxy-THC (THC-COOH), 11-hydroxy THC (11-OH-THC), THC-COOH/11-OH- THC ratio, 11-nor-9-carboxy-THC glucuronide (THC-COOGlu), cannabidol (CBD), cannbinol (CBN), cannabigerol (CBG), delta-9-tetrahydrocannabivarin (THCV), THCV-carboxylic acid, 11-nor-9-carboxy-delta-tetrahydrocannabivarin (THCV-COOH), albumin, apolipoproteins A1 and B (apoA1 and apoB), total protein, bilirubin, prolactin, triglycerides, creatinine, cortisol, glucose, lactate, Total 4, uric acid, blood urea nitrogen (BUN), blood sugar, calcium, ionized calcium, magnesium, sodium, phosphate, GABA, alcohol, aldehyde, and lactic acid.

The results from method (A) described above may be combined to produce a value or index of the biochemical profile, and the value, or index, may be used to determine if a threshold value has been obtained or exceeded, by comparing the value or index value against a reference value or reference index value, thereby indicating that the subject is positive for the corresponding physiological state, for example, intoxication.

If a positive result of intoxication for the subject is determined using the method (A) descried above, then the method as described above, may include a step of corrective action. For example, if the device (and optionally physiological parameters and behavioral parameters) is used for road-side testing of a driver of a car, then the operator of the test, for example a law enforcement officer, may perform corrective action and confiscate the car, suspend the driver's license, press charges and the like. Alternatively, if the device (and optionally physiological parameters and behavioral parameters) is used and corrective action is required, then operator of the test, for example a law enforcement officer or a health care provider, may forward the positive result indicating intoxication (impairment) to a third party so that corrective action may be taken. The result may be forwarded to the subject's employer if the subject is working within a high risk environment, for example as an air traffic controller, the subject is a pilot, the subject operates a commercial vehicle, the subject operates machinery (large or small) at a work site, or they are an operator at a nuclear power facility and the like.

Also described here is a method (B) of non-invasively determining a state of interest of being a subject comprising,
  (a) determining one or more than one physiological parameter of the subject;
  (b) placing a body part in contact with a receptor
  (c) directing a source of electromagnetic radiation (EMR) over a range of wavelengths through the receptor and onto body part so that the EMR reaches the blood and interstitial fluid within the body part;
  (d) measuring the EMR absorbed by, reflected by, or transmitted through, the blood and interstitial fluid of the body part with a detector to obtain a spectrum over the range of wavelengths;
  (e) performing a quantitative mathematical analysis of the spectrum using an algorithm to determine an amount of two or more than two analytes within the blood and interstitial fluid of the body part,
  (f) comparing the amount of the two or more than two analytes against a reference value of the two or more analytes to derive a biochemical profile, the biochemical profile and the one or more than one physiological parameter being used to determine the state of being in the subject.

In the method (B) described above, in the step of directing, the source of EMR is provided over a range of wavelengths from about 400 to about 2500 nm. The method may include a step of determining a behavioral parameter. Furthermore, the state of being of the subject may be a state of intoxication, for example if the state of being is:
  i) cannabis induced intoxication, then two or more than two analytes may include: delta-9-tetrahydrocannabinol (THC), THC glucuronide (THCGlu), 11-nor-9-carboxy-THC (THC-COOH), 11-hydroxy THC (11-OH-THC), THC-COOH/11-OH-THC ratio, 11-nor-9-carboxy-THC glucuronide (THC-COOGlu), cannabidol (CBD), cannbinol (CBN), cannabigerol (CBG), delta-9-tetrahydrocannabivarin (THCV), THCV-carboxylic acid, 11-nor-9-carboxy-delta-tetrahydrocannabivarin (THCV-COOH), albumin, apolipoproteins A1 and B (apoA1 and apoB), total protein, bilirubin, prolactin, triglycerides, creatinine, cortisol, glucose, lactate, Total 4, uric acid, blood urea nitrogen (BUN), blood sugar, calcium, ionized calcium, magnesium, sodium, phosphate, and GABA, the physiological parameter may include one or more of: heart rate, pulse rate, body temperature, neuropeptide Y, fatty acid amide hydrolase (FAAH), c reactive protein (cRP), creatine kinase (CK), aspartate amino transferase (AAT), asparate aminotransferase (AST), alanine transaminase (ALT), gamma-glutamyl transpeptidase (GGT), white blood cell count (WBC), red blood cell count (RBC), hemoglobin, hematocrit, neutrophils, lymphocytes, eosinophils, hypoactivity; THC in hair, THC in urine, and the one or more behavioral parameters may include determination of mental acuity (a name-face test, a fire alarm test, a two delayed recall tests, a misplaced objects test, a shopping list test, a digit symbol test), one or more motor skill test (a walk and turn test, a one leg stand test, a horizontal gaze nystagmus test, a divided attention test, a rhomberg balance test), the ability to function at a defined task, to operate machinery, drive an automobile, standardized field sobriety (Newmeyer, Swortwood, Taylor, et al., 2017, Clin Chem, 63(3), 647-662. doi:10.1373/clinchem.2016.265371);
  ii) alcohol induced intoxication, then two or more than two analytes may include: alcohol, aldehyde, lactic acid, the physiological parameter may include: heart rate, pulse rate, body temperature, neuropeptide Y, aspartate amino transferase (AAT), alanine transaminase (ALT), gamma-glutamyl transpeptidase (GGT), and the one or more behavioral parameters may include determination of mental acuity (a name-face test, a fire alarm test, a two delayed recall tests, a misplaced objects test, a shopping list test, a digit symbol test), one or more motor skill test (a walk and turn test, a one leg stand test, a horizontal gaze nystagmus test, a divided attention test, a rhomberg balance test), the ability to function at a defined task, to operate machinery, drive an automobile, standardized field sobriety; or
  iii) intoxication, for example resulting from a combination of cannabis and alcohol, or from opiates, fentanyl, amphetamines, phencyclidine, sedatives, anxyolytics, cocaine, caffeine, and nicotine consumption, then two or more than two analytes may include: delta-9-tetrahydrocannabinol (THC), THC glucuronide (THCGlu), 11-nor-9-carboxy-THC (THC-COOH), 11-hydroxy THC (11-OH-THC), THC-COOH/11-OH-THC ratio, 11-nor-9-carboxy-THC glucuronide (THC-COOGlu), cannabidol (CBD), cannbinol (CBN), cannabigerol (CBG), delta-9-tetrahydrocannabivarin (THCV), THCV-carboxylic acid, 11-nor-9-carboxy-delta-tetrahydrocannabivarin (THCV-COOH), albumin, apolipoproteins A1 and B (apoA1 and apoB), total protein, bilirubin, prolactin, triglycerides, creatinine, cortisol, glucose, Total 4, uric acid, blood urea nitrogen (BUN), blood sugar, calcium, ionized calcium, potassium, magnesium, sodium, phosphate, GABA, alcohol, aldehyde, and lactic acid, the physiological parameter may include one or more of: heart rate, pulse rate, body temperature, neuropeptide Y, fatty acid amide hydrolase (FAAH), c reactive protein (cRP), creatine kinase (CK), aspartate amino transferase (AAT), asparate aminotransferase (AST), alanine transaminase (ALT), gamma-glutamyl transpeptidase (GGT), white blood cell count (WBC), red blood cell count (RBC), total hemoglobin, hematocrit, neutrophils, lymphocytes, eosinophils, hypoactivity; THC in hair, THC in urine, and the one or more behavioral parameters may include determination of mental acuity (a name-face test, a fire alarm test, a two delayed recall tests, a misplaced objects test, a shopping list test, a digit symbol test), one or more motor skill test (a walk and turn test, a one leg stand test, a horizontal gaze nystagmus test, a divided attention test, a rhomberg balance test), the ability to function at a defined task, to operate machinery, drive an automobile, standardized field sobriety.

The results from method (B) described above may be combined to produce a value or index of the biochemical profile, the physiological parameter, the behavioral parameter, or a combination thereof, and these values, or index values, may be used to determine if a threshold value has been obtained or exceeded, by comparing the value or index value against a reference value or reference index value, thereby indicating that the subject is positive for the corresponding physiological state, for example, intoxication.

If a positive result of intoxication for the subject is determined using the method (B), described above, then the method as described above, may include a step of corrective action. For example, if the device (and optionally physiological parameters and behavioral parameters) is used for road-side testing of a driver of a car, then the operator of the test, for example a law enforcement officer, may perform corrective action and confiscate the car, suspend the driver's license, press charges and the like. Alternatively, if the device (and optionally physiological parameters and behavioral parameters) is used and corrective action is required, then operator of the test, for example a law enforcement officer or a health care provider, may forward the positive result indicating intoxication (impairment) to a third party so that corrective action may be taken. The result may be forwarded to the subject's employer if the subject is working within a high risk environment, for example as an air traffic controller, the subject is a pilot, the subject operates a commercial vehicle, the subject operates machinery (large or small) at a work site, or they are an operator at a nuclear power facility and the like.

As described herein there is also provided a device for detecting a physiological state of interest of a subject, comprising:
 a source of electromagnetic radiation (EMR) that emits a plurality of wavelengths of EMR from about 400 nm to about 2500 nm, the source of EMR being operatively coupled to a power source;
 a receptor sized to register with, and fit against, a sample, the receptor comprising one or more than one port;
 one or more than one input radiation guiding element in operable association with the source of EMR, one or more than one output radiation guiding element in operable association with a detector,
 the one or more than one input radiation guiding element and the one or more than one output radiation guiding element in optical alignment with the one or more than one port located and defining an EMR path within the receptor when the receptor is registered with, and fit against, the sample;
 the detector for measuring transmitted or reflected EMR received from the sample, the detector operatively coupled to a processing system;
 the processing system comprising one or more than one algorithm for determining a concentration for two or more than two analytes in the sample, and using the one or more than one algorithm to derive the physiological state of interest of the sample, wherein, the physiological state of interest is:
 i) cannabis induced intoxication, then two or more than two analytes may include: delta-9-tetrahydrocannabinol (THC), THC glucuronide (THCGlu), 11-nor-9-carboxy-THC (THC-COOH), 11-hydroxy THC (11-OH-THC), THC-COOH/11-OH-THC ratio, 11-nor-9-carboxy-THC glucuronide (THC-COOGlu), cannabidol (CBD), cannbinol (CBN), cannabigerol (CBG), delta-9-tetrahydrocannabivarin (THCV), THCV-carboxylic acid, 11-nor-9-carboxy-delta-tetra-hydrocannabivarin (THCV-COOH), albumin, apolipoproteins A1 and B (apoA1 and apoB), total protein, bilirubin, prolactin, triglycerides, creatinine, cortisol, glucose, lactate, Total 4, uric acid, blood urea nitrogen (BUN), blood sugar, calcium, ionized calcium, magnesium, sodium, phosphate, and GABA;
 ii) alcohol induced intoxication, then two or more than two analytes may include: alcohol, aldehyde, and lactic acid; or
 iii) intoxication, for example resulting from a combination of cannabis and alcohol, or from opiates, fentanyl, amphetamines, phencyclidine, sedatives, anxyolytics, cocaine, caffeine, and nicotine consumption, then two or more than two analytes may include: delta-9-tetrahydrocannabinol (THC), THC glucuronide (THCGlu), 11-nor-9-carboxy-THC (THC-COOH), 11-hydroxy THC (11-OH-THC), THC-COOH/11-OH-THC ratio, 11-nor-9-carboxy-THC glucuronide (THC-COOGlu), cannabidol (CBD), cannbinol (CBN), cannabigerol (CBG), delta-9-tetrahydrocannabivarin (THCV), THCV-carboxylic acid, 11-nor-9-carboxy-delta-tetra-hydrocannabivarin (THCV-COOH), albumin, apolipoproteins A1 and B (apoA1 and apoB), total protein, bilirubin, prolactin, triglycerides, creatinine, cortisol, glucose, lactate, Total 4, uric acid, blood urea nitrogen (BUN), blood sugar, calcium, ionized calcium, magnesium, sodium, phosphate, GABA, alcohol, aldehyde, and lactic acid.

The methods and device described herein permit the determination of a relative abundance of a range of compound or analytes of interest within a subject, which may be presented as a biochemical profile or fingerprint of the subject. The biochemical profile may be used to determine a physiological state of interest of a subject, for example an intoxicate state, an intoxicated state as a result of cannabis consumption (oral, inhalation, transdermal, or intravenous), an intoxicated state as a result of alcohol consumption, or an intoxicate state as a result of cannabis and alcohol consumption. The biochemical profile may also be combined with physiological parameters to determine the physiological state of interest of a subject. By developing a biochemical profile of the subject based on a plurality of analytes a more accurate determination of a state of being of the subject may be established when compared to previous methods that analyzed one or a few metabolites or compounds as an indicator of a physiological state.

As described herein, EMR is used to define a plurality of analytes quickly and without incremental cost and these results may be used to determine, or to assist in the determination (along with other data sets, for example, physiological, behavioral, or both, parameters), of a state of being. A state of being as determined using the methods described herein, may for example be a state of drug impairment that may necessitate action on the part of law enforcement officials and or the courts (for example, in the case of an impaired person operating a motor vehicle or piece of machinery).

This summary of the invention does not necessarily describe all features of the invention.

BRIEF DESCRIPTION OF THE DRAWINGS

These and other features of the invention will become more apparent from the following description in which reference is made to the appended drawings wherein.

DETAILED DESCRIPTION

Figure 1:
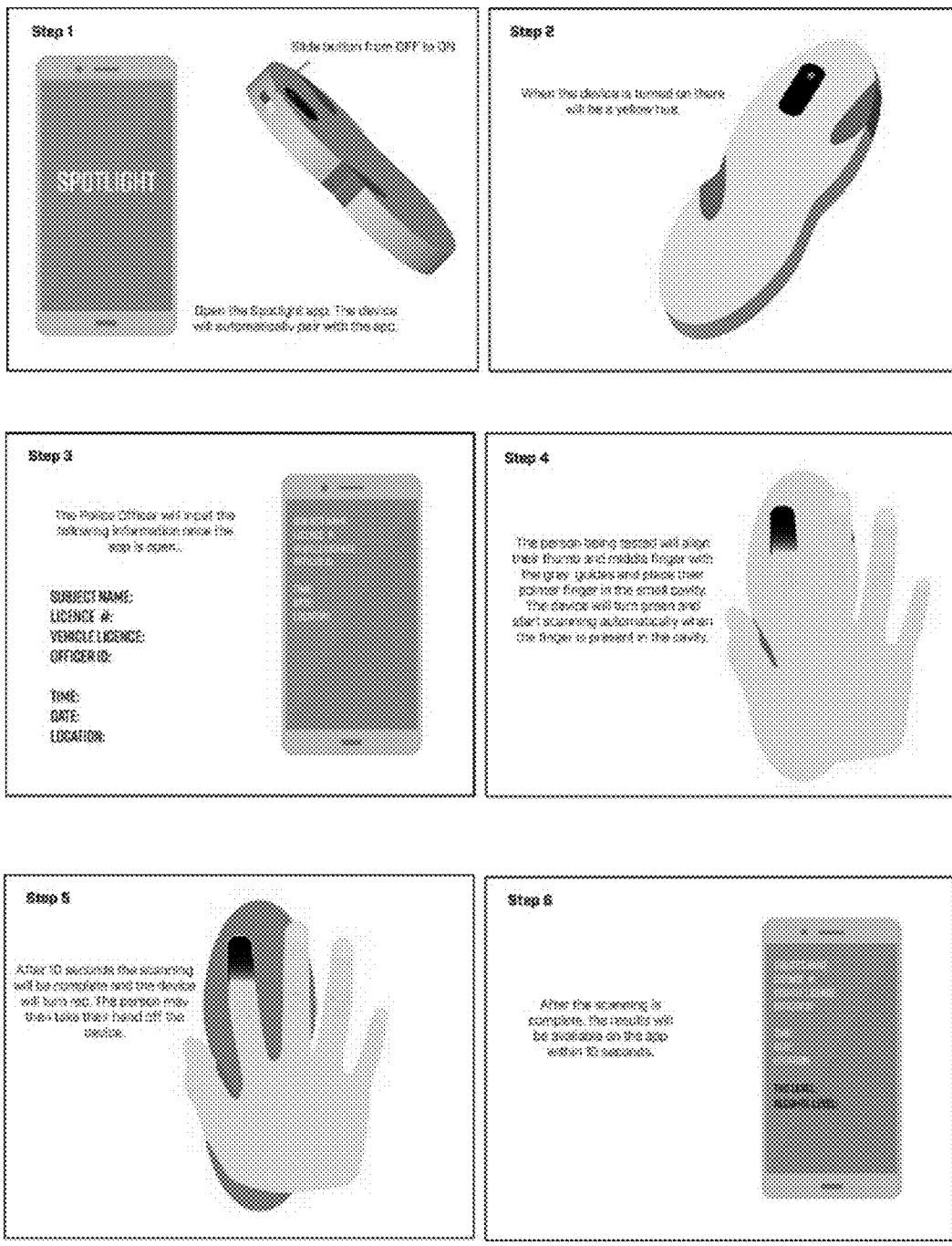
FIG. 1 shows an example of a device in accordance with an embodiment of the present invention

The present invention relates to non-invasive methods and a device for determining a physiological state of interest in a subject. The methods are used to determining biochemical profile or fingerprint, that is indicative of the physiological state of interest in the subject As used herein, the terms "comprising," "having," "including" and "containing," and grammatical variations thereof, are inclusive or open-ended and do not exclude additional, un-recited elements and/or method steps. The term "consisting essentially of" when used herein in connection with a use or method, denotes that additional elements and/or method steps may be present, but that these additions do not materially affect the manner in which the recited method or use functions. The term "consisting of" when used herein in connection with a use or method, excludes the presence of additional elements and/or method steps. A use or method described herein as comprising certain elements and/or steps may also, in certain embodiments consist essentially of those elements and/or steps, and in other embodiments consist of those elements and/or steps, whether or not these embodiments are specifically referred to. In addition, the use of the singular includes the plural, and "or" means "and/or" unless otherwise stated. The term "plurality" as used herein means more than one, for example, two or more, three or more, four or more, and the like. Unless otherwise defined herein, all technical and scientific terms used herein have the same meaning as commonly understood by one of ordinary skill in the art. As used herein, the term "about" refers to an approximately +/−10% variation from a given value. It is to be understood that such a variation is always included in any given value provided herein, whether or not it is specifically referred to. The use of the word "a" or "an" when used herein in conjunction with the term "comprising" may mean "one," but it is also consistent with the meaning of "one or more," "at least one" and "one or more than one."

The expression "body part" or "part of a subject", as used herein, refers to an element or section of a human to which electromagnetic radiation (EMR) can be directed. The element or section can be, for example, an earlobe, a finger, an arm, a leg, torso, cheek, or a toe.

Described herein are non-invasive methods for determining a physiological state of interest in a subject. For example, the method may involve placing a body part in contact with a receptor of a device. Directing a source of electromagnetic radiation (EMR) over a range of wavelengths, for example from about 400 to about 2500 nm, through the receptor and onto body part so that the EMR reaches the blood and interstitial fluid within the body part, and measuring the EMR absorbed by, reflected by, or transmitted through, the blood and interstitial fluid of the body part with a detector to obtain a spectrum over the range of wavelengths. A quantitative mathematical analysis of the spectrum is performed using an algorithm that determines an amount of two or more than two analytes within the blood and interstitial fluid of the body part. The amount (for example, the concentration or level) of the two or more than two analytes are used to derive a biochemical profile, or fingerprint of the subject.

The amount of the two or more than two analytes (the biochemical fingerprint also termed biochemical profile) may be compared against reference values of the two or more analytes obtained from reference (control) subjects, for example, from a cross section of healthy individuals in order to provide data that may be used to indicate the status of a physiological state of interest of the subject. Additionally, the biochemical fingerprint (biochemical profile) may be monitored over time and compared against previous values of the two or more analytes obtained from the same subject in order to obtain data that may be used to manage the physiological state of interest, of the subject.

The biochemical profile may also be combined with physiological parameters to determine the physiological state of interest, of a subject. The "state of being" may include a physiological state of interest for example as a result of intoxication, for example but not limited to intoxication arising from cannabis consumption, alcohol consumption, both cannabis and alcohol consumption, or from the consumption of other intoxicants, for example but not limited to consumption of opiates, fentanyl, amphetamines, phencyclidine, sedatives, anxyolytics, cocaine, caffeine, and nicotine.

The device as described herein may be used to determine if the physiological state of interest of a subject is indicative of a state of intoxication. If a state of intoxication is determined, then corrective action may be taken directly, or the result of the test may be forwarded to another party so that corrective action may be taken by the other party. For example, if the device is used for road-side testing, and the operator of the device (and optionally delivering the physiological and behavioral tests) is a law enforcement officer and a result is obtained that is indicative of a state of intoxication for the driver or a car, then the operator of the test, for example the law enforcement officer, may perform corrective action and confiscate the car, suspend the driver's license, press charges and the like. Alternatively, the operator of the test, a health care worker, or the law enforcement officer, may forward the positive result indicating intoxication (impairment) to a third party, for example a justice of the peace, and corrective action may be taken. In some circumstances, for example, where safety is a requirement of the subjects employment, if the subject has been determined to exhibit a positive result indicating intoxication (impairment), then the result may be forwarded to the subject's employer. Examples of situations where safety may be a requirement of the subjects employment, include if the subject is working as an air traffic controller, the subject is a pilot, they operate a commercial vehicle, they operate machinery (large or small) at a work site, they are an operator at a nuclear power facility etc.

By consumption it is meant that the intoxicant, for example, but not limited to, cannabis, alcohol, opiates, fentanyl, amphetamines, phencyclidine, sedatives, anxyolytics, cocaine, caffeine, nicotine, enters, is taken, or is administered to, or by, the subject orally (for example as an edible product), by inhalation (for example, via smoking, an e-cigarette, via a hookah, via an oral spray, snorting, or using an aspirator or inhaler), by transdermal delivery (for example, via a patch, cream, spray, or oil), or intravenously (for example by injection or as a drip solution), or other method.

The physiological state of interest may be detected or defined on the basis of two or more than two metabolites (also termed analytes) and optionally, one or more physiological parameter, or one or more behavioral parameter, or the physiological state of interest may be defined using two or more than two analytes, and both the one or more physiological parameter, and the one or more behavioral parameter. While a state of being may be described using a plurality of metabolites (analytes), these results may be combined with physiological parameter(s), and/or behavioral parameters, to further define the state of being. The metabolites may be determined to have, or not to have, an interdependent role in the state of being. The metabolites, the physiological parameters, or both the metabolites, the physiological parameters may be termed "variables" and these variables may be used to describe the state of being, or these variables considered as markers representative of the state of being. By using multiple metabolites combined with other physiological variables that are correlated in some manner to the physiological state of interest, a more accurate determination of the physiological state of interest may be obtained when compared to determining the physiological state of interest determined using one analyte.

The methods described herein permit management of multiple variables or markers that are correlated with, and that may have an influence on, the physiological state of interest, and therefore can be used to characterize and determine the physiological state of interest of a subject or patient.

A fingerprint indicative of a physiological state resulting from intoxication may be determined using a plurality of metabolites, and one or more physiological parameter, and/or one or more behavioral parameter. These variables (metabolites, and physiological parameters and/or behavioral parameters), may be compared to base-line values that have been determined from healthy individuals, and any deviation from the base-line values is indicative of the physiological state of interest, of the subject. These metabolites, and physiological parameters and/or behavioral parameters may be also compared to values determined overtime from the same subject, and any deviation from the time-course values of these variable, (or markers) may indicates a change in the physiological state of interest in the subject. Therefore, the measured biochemical fingerprint, and physiological parameters and/or behavioral parameters, may be used to monitor, and manage, the physiological state of interest over time.

Non-limiting examples of a physiological state of interest in the subject may include but are not limited to: intoxication, for example as a result of cannabis consumption, alcohol consumption, both cannabis and alcohol consumption, or from the consumption of other intoxicants, for example but not limited to consumption of opiates, fentanyl, amphetamines, phencyclidine, sedatives, anxyolytics, cocaine, caffeine, and nicotine. Non-limiting examples of metabolites that may be determined to obtain a biochemical fingerprint of the corresponding physiological state of interest include (also see Table 1):

i) intoxication (cannabis induced): the two or more than two analytes may include: delta-9-tetrahydrocannabinol (THC), THC glucuronide (THCGlu), 11-nor-9-carboxy-THC (THC-COOH), 11-hydroxy THC (11-OH-THC), THC-COOH/11-OH-THC ratio, 11-nor-9-carboxy-THC glucuronide (THC-COOGlu), cannabidol (CBD), cannbinol (CBN), cannabigerol (CBG), delta-9-tetrahydrocannabivarin (THCV), THCV-carboxylic acid, 11-nor-9-carboxy-delta-tetrahydrocannabivarin (THCV-COOH), albumin, apolipoproteins A1 and B (apoA1 and apoB)), total protein, bilirubin, prolactin, triglycerides, creatinine, cortisol, glucose, lactate, Total 4, uric acid, blood urea nitrogen (BUN), blood sugar, calcium, ionized calcium, magnesium, sodium, phosphate, and gamma-aminobutyric acid (GABA);

ii) alcohol induced intoxication, then two or more than two analytes may include: alcohol, aldehyde, and lactic acid; or iii) intoxication generally, for example arising from a combination of cannabis and alcohol, or from opiates, fentanyl, amphetamines, phencyclidine, sedatives, anxyolytics, cocaine, caffeine, and nicotine consumption, then two or more than two analytes may include: then two or more than two analytes may include: delta-9-tetrahydrocannabinol (THC), THC glucuronide (THCGlu), 11-nor-9-carboxy-THC (THC-COOH), 11-hydroxy THC (11-OH-THC), THC-COOH/11-OH-THC ratio, 11-nor-9-carboxy-THC glucuronide (THC-COOGlu), cannabidol (CBD), cannbinol (CBN), cannabigerol (CBG), delta-9-tetrahydrocannabivarin (THCV), THCV-carboxylic acid, 11-nor-9-carboxy-delta-tetrahydrocannabivarin (THCV-COOH), albumin, apolipoproteins A1 and B (apoA1 and apoB), total protein, bilirubin, prolactin, triglycerides, creatinine, cortisol, glucose, lactate, Total 4, uric acid, blood urea nitrogen (BUN), blood sugar, calcium, ionized calcium, magnesium, sodium, phosphate, GABA, alcohol, aldehyde, and lactic acid.

TABLE 1

Non-limiting examples of analytes and physiological parameters that may be used to determine intoxication as described herein

| | Description | Influence |
|---|---|---|
| C-reactive Protein | C-reactive protein (CRP) is an acute phase protein that increases in the blood with inflammation and infection such as following a heart attack, surgery, or trauma. CRP may be used to indicate a change in the level of stress in a subject. | High |
| Creatinine (IDMS) | Measures the level of creatinine in the blood. Creatinine is a waste product that forms when creatine (found in muscle), breaks down. For example: dehydration. This analyte may be used as a measurement of kidney function. | Medium |
| Glucose | A blood glucose test measures the amount of glucose in your blood plasma. Cannabis use can reduce the amount of glucose in blood. | High |
| BUN | A blood urea nitrogen (BUN) test measures the amount of nitrogen in your blood that comes from the waste product urea. Urea is made when protein is broken down in your body. May be used to assess kidney function. | Low |
| THC | THC | High |
| Total Protein | A total serum protein test measures the total amount of protein in the blood. It also measures the amounts of two major groups of proteins in the blood: albumin and globulin. | Low |
| Albumin | A plasma binding protein synthesized by the liver. Albumin helps to maintain osmotic pressure in the vascular space and also reflects overall nutritional status. It is also assists in transport of various substances throughout your body, including hormones, vitamins, and enzymes. | High |
| Prolactin | A prolactin (PRL) test measures how much of a hormone called prolactin you have in your blood. The hormone is made in your pituitary gland, which is seated at the base of the brain. It is known to be affected by physiological stress, which is known to be a factor in THC impairment. | High |
| Potassium | It is mostly found intracellularly, and less so interstitially and in serum. It can be used to diagnose and monitor kidney disease, high blood pressure, and heart disease. | Low |
| Sodium | Is a cation found mainly in extracellular fluid and may be used to evaluate sate of hydration. Sodium, along with other electrolytes such as potassium, chloride, and bicarbonate (or total $CO_2$) may be used to evaluate metabolic acidosis. Excess alcohol ingestion is known to cause ketoacidosis. Sensitive but not specific. | High |
| Cortisol | A steroid hormone produced by the adrenal cortex. It is used to evaluate pituitary or adrenal function. It is known to be effected by stress. Sensitive but not specific. | High |
| Lactate | An intermediate breakdown product of glucose metabolism primarily from anaerobic metabolism in muscle. Lactic acid levels increases as a result of strenuous exercise, heart failure, a severe infection (sepsis), or shock. Lactic acidosis results when there is oxygen deprivation in the tissues. Lactate may be used as an indirect estimation of oxygenation, and to evaluate metabolic acidosis. Acute phase reaction. Sensitive and potentially specific. | Low |
| Total T4 | A hormone secreted by the thyroid gland. Total T4 is converted into another thyroid hormone (T3; triiodothyronine). Any change show up in T4 first. T3 and T4 help to control how body stores and uses energy (metabolism). Sensitive but not specific. | High |
| Calcium, ionized calcium | The sum of calcium plus protein bound calcium, ionized calcium. It is important in cellular transport mechanisms. The most common cause for low calcium, ionized calcium is low albumin/protein. Sensitive but not specific. | High |
| Uric Acid | Uric acid is an end product of purine metabolism. High levels can be associated with gout and hypothyroidism. Cannabis is known to lower the level of uric acid. Sensitive and specific. | High |

TABLE 1-continued

Non-limiting examples of analytes and physiological parameters that may be used to determine intoxication as described herein

| | Description | Influence |
|---|---|---|
| Triglyceride | Triglycerides are a dominant form of fat in the body. They are insoluble in blood. Their levels may be elevated with high alcohol consumption and immediate high consumption of carbohydrates, such as junk foods. Sensitive and potentially specific. | High |
| Magnesium | An important cation involved in cellular and bone metabolism. It's needed for proper muscle, nerve, and enzyme function. It also helps the body make and use energy. Alcohol abuse lowers the level. Sensitive and potentially specific. | High |
| Creatine Kinase | An enzyme found in the cardiac and skeletal muscle, brain and lung. Levels of CK can rise after a heart attack, skeletal muscle injury, strenuous exercise, and from taking certain medicines or supplements. Sensitive and potentially specific. | High |
| GGT | Gamma-glutamyl transferase (GGT) is an enzyme that is found in many organs throughout the body, with the highest concentrations found in the liver. It is sensitive to acute alcohol ingestion. Smoking may cause elevated GGT levels. Acute phase reactor. Highly sensitive and potentially specific. | High |
| AST | The aspartate aminotransferase (AST) is mainly found in the liver but it is also found in muscle and kidney. It is involved in amino acid metabolism. It is used to assess liver damage, such as with alcohol abuse. Slow responder. | Low |
| Total Bilirubin | A breakdown product of hemoglobin. It is used to assess liver function. Sensitive but not specific. | Low |
| WBC Count | The number of white blood cells (WBC) per ml of blood. WBC's primarily consist of neutrophils, lymphocytes, monocytes, eosinophils, and basophils. WBC's are mobilized by inflammation and infection. Sensitive but not specific. | High |
| RBC Count | The number of red blood cells (RBC) per cubic ml of whole blood. This measure is lower with alcohol abuse. | Low |
| Hemoglobin | Oxygen carrying protein found in RBCs. It is lowered by alcohol abuse. Sensitive but not specific. | High |
| Hematocrit | The hematocrit blood test determines the percentage of blood volume composed of red blood cells (RBC's). Used to diagnose anemia. | Medium |
| Neutrophils | A type of granulocytic WBC. They are involved in inflammatory reactions and function as a primary defence against acute infections. Stress and smoking can elevate levels of neutrophils. Sensitive and not specific. | High |
| Lymphocytes | Small white blood cells consisting of B lymphocytes that control antibody response and T lymphocytes that control cell mediated response. Sensitive and not specific. | Medium |
| Eosinophils | Subclass of WBC granulocytes. Involved in allergic reactions and in attacking parasites. | Medium |

Another example of a method for non-invasively determining a physiological state of interest of a subject involves determining the biochemical profile (or fingerprint) as outlined above, along with determining one or more than one physiological parameter of the subject and using the biochemical profile and one or more than one physiological parameter to determine the physiological state of interest, of the subject. In this method, the biochemical profile is determined by placing a body part in contact with a receptor and directing a source of electromagnetic radiation (EMR) over a range of wavelengths, for example from about 400 to about 2500 nm, through the receptor and onto body part so that the EMR reaches the blood and interstitial fluid within the body part. The EMR that is absorbed by, reflected by, or transmitted through, the blood and interstitial fluid of the body part is measured with a detector in order to obtain a spectrum over the range of wavelengths, and a quantitative mathematical analysis of the spectrum is performed using an algorithm to determine an amount of two or more than two analytes within the blood and interstitial fluid of the body part. The amount of the two or more than two analytes are used to derive a biochemical profile, which may be compared against reference values of the two or more analytes. The biochemical profile and the one or more than one physiological parameter may be used to determine the state of being, physiological state of interest for example intoxication as described herein.

In addition to determining a biochemical profile and one or more than one physiological parameter, one or more behavioral parameters may also be determined to characterize the physiological state of interest. Non-limiting examples of behavioral parameters that may be evaluated include, determination of mental acuity (for example but not limited to a name-face test, a fire alarm test, a two delayed recall tests, a misplaced objects test, a shopping list test, a digit symbol test), one or more motor skill test (for example but not limited to, a walk and turn test, a one leg stand test, a horizontal gaze nystagmus test, a divided attention test, a rhomberg balance test), the ability to function at a defined task, for example to operate machinery, drive an automobile (or use a driving simulator), state of physical fitness, standardized field sobriety (Newmeyer, Swortwood, Taylor, et al., 2017, Clin Chem, 63(3), 647-662. doi:10.1373/clinchem.2016.265371), and the like.

For example, a driving simulator, is known to be useful in assessing on-the-road driving tests (Micallef et al., 2018, Fundam Clin Pharmacol. doi:10.1111/fcp.12382) and the simulator may be used as a test in place of driving an automobile). Studies with standardized and objective measures of driving using driving simulators have found impairments in driving following moderate cannabis intake (e.g. 8% THC; in a 500-750 mg cigarette, approximately 40-60 mg of THC). Reported effects include increased weaving, decreased speed, decreased steering control, longer reaction time and, increased headway (Hartman et al., 2015, Drug Alcohol Depend, 154, 25-37. doi:10.1016/j.drugalcdep.2015.06.015; Lenne et al., 2010, Accid Anal Prev, 42(3), 859-866. doi:10.1016/j.aap.2009.04.021; Micallef et al., 2018, Fundam Clin Pharmacol. doi:10.1111/fcp.12382; Anderson, et al., 2010, J Psychoactive Drugs, 42(1), 19-30. doi:10.1080/02791072.2010.10399782; Ronen et al., 2010, Accid Anal Prev, 42(6), 1855-1865. doi:10.1016/j.aap.2010.05.006; Ronen et al., 2008, Accid Anal Prev, 40(3), 926-934. doi:10.1016/j.aap.2007.10.011).

In the case where there is an interrogation of a physiological state of interest, a behavioral parameter data may also be combined with the biochemical profile and physiological parameters to further assist in determining the degree or status of the physiological state of interest. For example, the data (the tested values) may be combined to determine if the subject has surpassed a threshold value, index, ratio, or set of values, and/or, the degree, or the extent to which the subject is exhibiting the physiological state of interest, for example the degree of intoxication. The baseline values that are used to determine the index, ratio, or set of values, against which the tested values are compared, are determined from normalized healthy subjects, analyzed under control conditions.

Non-limiting examples of a physiological state of interest include intoxication arising from cannabis, alcohol, opiates, fentanyl, amphetamines, alcohol, phencyclidine, sedatives, anxyolytics, cocaine; caffeine-induced disorders; and nicotine-induced disorders. For example:

i) if the intoxication is cannabis-induced, then the two or more than two analytes may include: delta-9-tetrahydrocannabinol (THC), THC glucuronide (THCGlu), 11-nor-9-carboxy-THC (THC-COOH), 11-hydroxy THC (11-OH-THC), THC-COOH/11-OH-THC ratio, 11-nor-9-carboxy-THC glucuronide (THC-COOGlu), cannabidol (CBD), cannbinol (CBN), cannabigerol (CBG), delta-9-tetrahydrocannabivarin (THCV), THCV-carboxylic acid, 11-nor-9-carboxy-delta-tetrahydrocannabivarin (THCV-COOH), albumin, apolipoproteins A1 and B (apoA1 and apoB), total protein, bilirubin, prolactin, triglycerides, creatinine, cortisol, glucose, lactate, Total 4, uric acid, blood urea nitrogen (BUN), blood sugar, calcium, ionized calcium, magnesium, sodium, phosphate, and GABA, the physiological parameter may include one or more of: heart rate, pulse rate, body temperature, neuropeptide Y, fatty acid amide hydrolase (FAAH), c reactive protein (cRP), creatine kinase (CK), aspartate amino transferase (AAT), asparate aminotransferase (AST), alanine transaminase (ALT), gamma-glutamyl transpeptidase (GGT), white blood cell count (WBC), red blood cell count (RBC), hemoglobin, hematocrit, neutrophils, lymphocytes, eosinophils, hypoactivity; THC in hair, and THC in urine, and the one or more behavioral parameters may include determination of mental acuity (a name-face test, a fire alarm test, a two delayed recall tests, a misplaced objects test, a shopping list test, a digit symbol test), one or more motor skill test (a walk and turn test, a one leg stand test, a horizontal gaze nystagmus test, a divided attention test, a rhomberg balance test), the ability to function at a defined task, to operate machinery, drive an automobile, standardized field sobriety;

ii) for alcohol-induced intoxication, then two or more than two analytes may include: alcohol, aldehyde, lactic acid, the physiological parameter may include: heart rate, pulse rate, body temperature, neuropeptide Y, aspartate amino transferase (AAT), alanine transaminase (ALT), gamma-glutamyl transpeptidase (GGT), and the one or more behavioral parameters may include determination of mental acuity (a name-face test, a fire alarm test, a two delayed recall tests, a misplaced objects test, a shopping list test, a digit symbol test), one or more motor skill test (a walk and turn test, a one leg stand test, a horizontal gaze nystagmus test, a divided attention test, a rhomberg balance test), the ability to function at a defined task, to operate machinery, drive an automobile, standardized field sobriety; or iii) for intoxication, for example resulting from cannabis and alcohol, or opiates, fentanyl, amphetamines, phencyclidine, sedatives, anxyolytics, cocaine, caffeine, and nicotine consumption, then two or more than two analytes may include: then two or more than two analytes may include: delta-9-tetrahydrocannabinol (THC), THC glucuronide (THCGlu), 11-nor-9-carboxy-THC (THC-COOH), 11-hydroxy THC (11-OH-THC), THC-COOH/11-OH-THC ratio, 11-nor-9-carboxy-THC glucuronide (THC-COOGlu), cannabidol (CBD), cannbinol (CBN), cannabigerol (CBG), delta-9-tetrahydrocannabivarin (THCV), THCV-carboxylic acid, 11-nor-9-carboxy-delta-tetrahydrocannabivarin (THCV-COOH), albumin, apolipoproteins A1 and B (apoA1 and apoB), total protein, bilirubin, prolactin, triglycerides, creatinine, cortisol, glucose, lactate, Total 4, uric acid, blood urea nitrogen (BUN), blood sugar, calcium, ionized calcium, magnesium, sodium, phosphate, GABA, alcohol, aldehyde, and lactic acid, the physiological parameter may include one or more of: heart rate, pulse rate, body temperature, neuropeptide Y, fatty acid amide hydrolase (FAAH), c reactive protein (cRP), creatine kinase (CK), aspartate amino transferase (AAT), asparate aminotransferase (AST), alanine transaminase (ALT), gamma-glutamyl transpeptidase (GGT), white blood cell count (WBC), red blood cell count (RBC), hemoglobin, hematocrit, neutrophils, lymphocytes, eosinophils, hypoactivity; THC in hair, THC in urine, and the one or more behavioral parameters may include determination of mental acuity (a name-face test, a fire alarm test, a two delayed recall tests, a misplaced objects test, a shopping list test, a digit symbol test), one or more motor skill test (a walk and turn test, a one leg stand test, a horizontal gaze nystagmus test, a divided attention test, a rhomberg balance test), the ability to function at a defined task, to operate machinery, drive an automobile, standardized field sobriety (Newmeyer, Swortwood, Taylor, et al., 2017, Clin Chem, 63(3), 647-662. doi:10.1373/clinchem.2016.265371).

After the data is collected by the device as described herein, the result can be stored, shown on a display, or transmitted to another central CPU for further analysis or display. For example, the data may be transmitted to a central computer that analyses the measured metabolites, in combination with the measured physiological parameters and if desired measured behavioral parameters, in order to determine an overall index of the physiological state for the subject (patient). For example, the collected data may be compared with known data sets previously obtained for the physiological state of interest, and the "index value" determined. The index value may range for example from 0 (the patent is in a sever intoxicated state for the physiological state of interest being analyzed) to 1 (the patient is in an normal or healthy state for the physiological state of interest).

Figure 2:
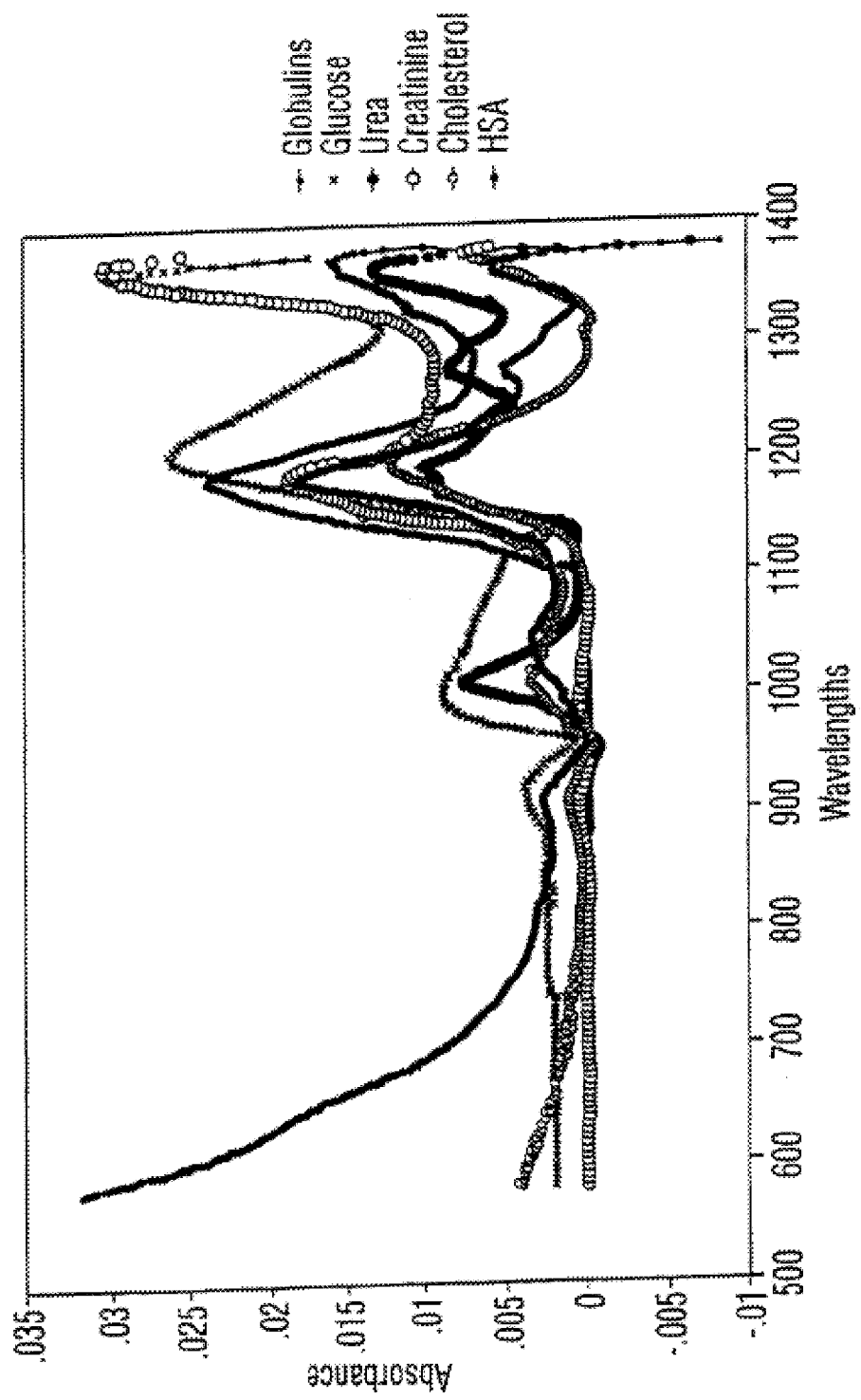
FIG. 2 is prior art (U.S. Pat. No. 6,657,717) and shows the absorbance spectra for globulins, glucose, urea, creatinine, cholesterol and HAS over a range of wavelengths from 500 nm to 1400 nm.
Figure 3:
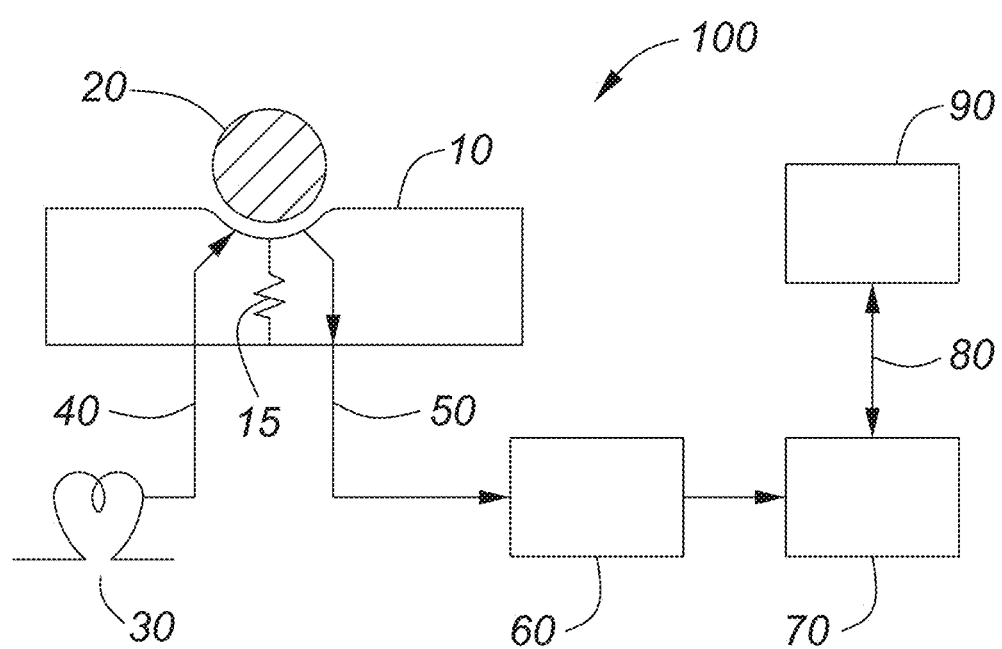
FIG. 3 shows a schematic view of a device according to an embodiment of the present invention.

With reference to FIG. 3, the apparatus or device 100 that may be used in the methods described herein, comprises a receptor (also termed primary receptor) 10 shaped so that it can be placed in contact with a region of skin or a body part from a subject 20. A source electromagnetic radiation (EMR; 30) is directed 40 into the receptor 10, and following interaction with two or more than two compounds within the body part 20, the EMR is collected 50 and analyzed. The apparatus 100 may be as shown in FIG. 1, or it may be based on an apparatus as known in the art, for example, but not limited to those disclosed in US 2013/0248695, U.S. Pat. Nos. 5,361,758, 5,429,128, WO 93/16629, U.S. Pat. Nos. 6,236,047 6,040,578 or 6,240,306 (all of which are incorporated herein by reference). The EMR 50 that is collected after interaction with compounds within the body part of the subject 20 may be either reflected from, transmitted through, absorbed by, or a combination thereof, the body part of the subject 20 depending upon the apparatus used. The collected EMR signal is directed to a spectrometer 60 and the data processed 70 using one or more than one calibration algorithms to determine the concentration of two, or more than two target compounds within the body part 20, to derive a biochemical profile, and determine the physiological condition or status of the subject. If desired, the data may be transferred wirelessly or by wire 80 to another device 90, for example a cell phone, or an off-site CPU, that comprises a program that can collect the data, display the results or a combination thereof. A non-limiting example of spectra of a range of compounds in blood, and measured non-invasively, is shown in FIG. 2.

The apparatus 100 as shown in FIG. 1 may further comprise a strap attached to the device. The strap may assist in maintaining control of the device while the test is being administered.

In order to minimize the effects of scatter associated with incorrect pressure applied to the receptor during measurement, the device 100 may comprise a pressure sensor 15 positioned around, under, or adjacent to, receptor (primary receptor) 10. If present, the pressure sensor is used to determine if there is too little, or too much, pressure between the skin surface that is placed against the receptor, and the receptor itself. For example, if there is too little or too much pressure against receptor 10 a signal from the pressure sensor 15 may be used to illuminate the bottom section of the device thereby signaling the need for correction and re-adjustment of the body part against the receptor.

Figure 4:
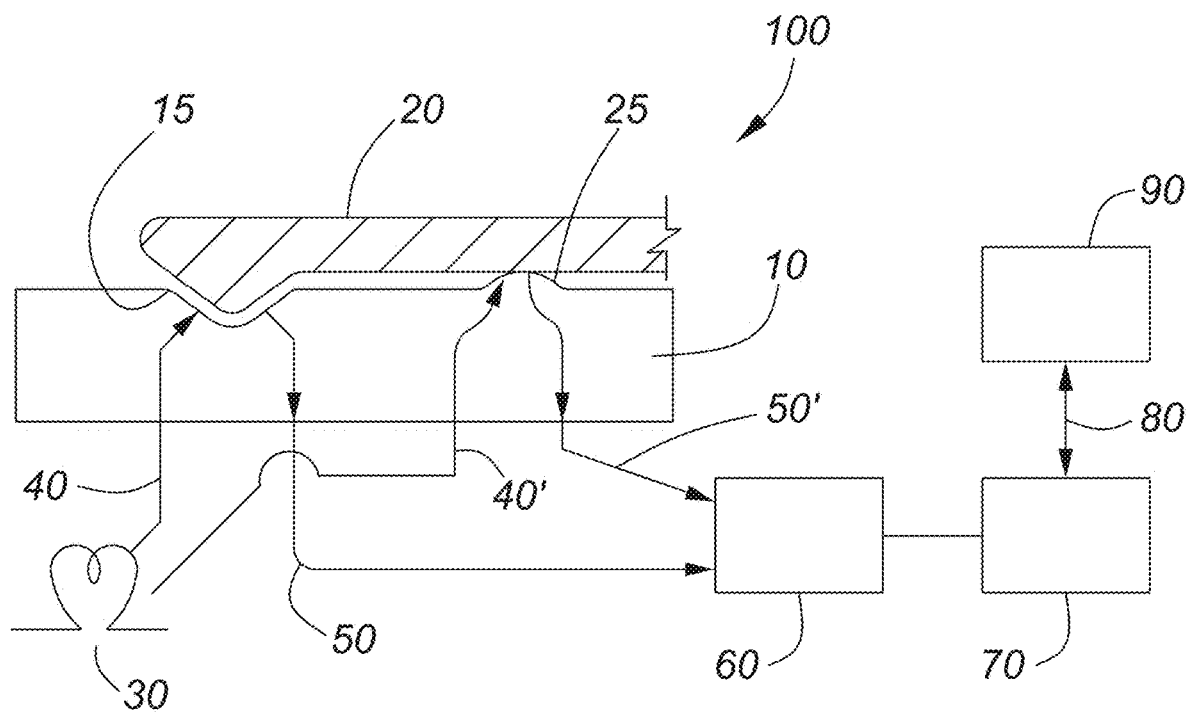
FIG. 4 shows a schematic view of a device according to an embodiment of the present invention.

The device 100 may comprise more than one receptor. For example, which is not to be considered limiting, when a body part 20, for example an index finger, is being measured by device 100, a second body part, for example the palm of the hand may be positioned over the device so that the second body part may press against the device while the subject is having their first body part measured. In this example, as shown in FIG. 4, device 100 may comprise primary receptor 10 and a secondary receptor 25 located at a location where the second body part may press against the secondary receptor 25.

The secondary receptor 25 may be configured in a similar manner as that of primary receptor 10, so that the EMR 50' collected after interaction with compounds within the second body part of the subject that are either reflected from, transmitted through, absorbed by, or a combination thereof, is used to determine the presence of the same or another analyte. In the example shown in FIG. 4, the source of EMR 30 is shown as being the same for both the primary 15 and the secondary 25, receptor. In this example, the EMR source may emit a range of wavelengths that may be used to determine the occurrence of one or several analytes within the first and second body parts. For example, if the physiological state of being is intoxication, a first measured analyte, or group of first measured analytes, may be those related to cannabis-induced intoxication as described above, while a second analyte or a second set of analytes may be those related to alcohol-induced intoxication, as described above. If desired, the set of wavelengths emitted by the EMR 30 may also be used to determine the presence of a third analyte or set of analytes, associated with another physiological state of being, for example, opioid-induced intoxication. The third analyte or set of analytes may be interrogated using a third set of wavelengths, the range of these wavelengths may overlap, or be distinct from, the first and/or second set of wavelengths. The third set of wavelengths may be directed to either the first receptor, or the second receptor, or the third set of wavelengths may be directed to a third receptor that is placed within device 100 so that the third receptor contacts a third body part when the body part, for example a hand, is placed on device 100.

Alternatively, separate sources of EMR may be directed to a first receptor and a second receptor in the device 100. For example, one source of EMR, for example a first LED, emitting wavelengths of EMR within a first range of wavelengths, may be directed via optic fiber 40 to primary receptor 15, and a second source of EMR, for example a second LED that emits wavelengths of EMR within a second range of wavelengths, may be directed via optic fiber 40' to secondary receptor 25. In this configuration, the first set of wavelengths and the second set of wavelengths are different, and the range of wavelengths may overlap, or the range of wavelengths may be distinct, and the device 100 may determine the presence of different analytes within each of the first and second body parts. For example, if the physiological state of being is intoxication, a first measured analyte, or group of first measured analytes, may be those related to cannabis-induced intoxication as described above, while a second analyte or a second set of analytes may be those related to alcohol-induced intoxication, as described above. In a similar manner as noted above, if desired, a third set of wavelengths emitted by the EMR 30 may be used to determine the presence of a third analyte or set of analytes, associated with a third physiological state of being, for example associated with opioid-induced intoxication. In this example, the third set of wavelengths, having a range of wavelengths that may overlap, or be distinct from, the first or second set of wavelengths, may be directed to either the first or second receptors, or the third set of wavelengths may be directed to a third receptor that is also configured within device 100 to touch a third body part.

The primary receptor 10, and the second receptor 25 (and if present the third receptor), of the present invention may each be comprised of a single sided probe that can make contact with a skin sample. Such a probe may comprise concentric rings of optic fibers so that each ring is made up by fibers carrying either input or output EMR. If the inner ring of fibers is carrying input EMR, then the outer ring of fibers may carry the output signal, or visa versa. Alternatively, the probe may comprise one or more input optic fibers and a separate set of output optic fibers positioned adjacent the input set of fibers. This type of probe may be used to determine the concentration of two or more than two compounds within the blood and interstitial fluid using reflectance, absorbance, and/or transmittance. During use, the probe may be placed against the skin of the finger, hand, arm, back or elsewhere (see FIG. 1).

Alternate configurations of an apparatus may also be used for the determination of a compound within a part, as described herein, including, but not limited to those described in US 2013/0248695, U.S. Pat. No. 5,361,758, WO 93/16629, U.S. Pat. Nos. 6,236,047, 5,429,128, 6,040,578 or U.S. Pat. No. 6,240,306 (all of which are incorporated herein by reference), with modification of the calibration algorithms so that they may be used to determine the concentration of two or more than two compounds of interest within each body part, deriving a biochemical profile, and determining a physiological condition of a the subject, as described herein.

The present invention provides a method to develop an algorithm that accounts for the differences in concentration of two or more than two compounds within the body part. For example, which is not to be considered limiting, if one of the compounds (or analytes, or metabolites) is glucose, then the concentration of glucose within each of the blood, and the interstitial fluid may be determined. From these values a reference measurement for glucose may be determined, and this reference value used to develop an algorithm. Absorbance values of a body part may be obtained over a set of wavelengths set as a dependent variable, and glucose reference measurement used as an independent variable. These values can then be processed using any suitable statistical procedure, including but not limited to, Partial Least Squares or Multiple Linear Regression to produce an algorithm for blood glucose. This procedure can be repeated for any compound or analyte of interest for which a concentration within blood and/or interstitial fluid is desired.

The concentration of a given compound may be calculated according to the present invention by using a calibration equation derived from a statistical analysis, for example but not limited to a least squares best fit, of a plot of the values of concentration of a calibration set of samples of the compound, which are determined using the method of the present invention, versus the values of the concentration of the calibration set measured directly by a different method. However, it si to be understood that other statistical tests may be used was known in the art, for example but not limited to multiple linear regression (MLR), partial least squares (PLS), and the like. Any known method for determining the concentration of one, or more than one, compound may be used as would be known to one of skill in the art.

In the case of glucose, as an example, and which is not to be considered limiting, blood glucose levels can be readily determined using well known in vitro techniques as known in the art. The level of glucose in the interstitial compartment may be determined using reverse ionotophoesis. In the case of THC and related metabolites, for example but not limited to, delta-9-tetrahydrocannabinol (THC), THC glucuronide (THCGlu), 11-nor-9-carboxy-THC (THC-COOH), 11-hydroxy THC (11-OH-THC), THC-COOH/11-OH-THC ratio, 11-nor-9-carboxy-THC glucuronide (THC-COOGlu), cannabidol (CBD), cannbinol (CBN), cannabigerol (CBG), delta-9-tetrahydrocannabivarin (THCV), THCV-carboxylic acid, 11-nor-9-carboxy-delta-tetrahydrocannabivarin (THCV-COOH) levels can be readily determined using well known in vitro techniques as known in the art, for example using liquid chromatography and tandem mass spectrometry (Schwope D., et. al., 2011, Anal. Bioanal Chem. 410:1273-1283), or GC-MS (Marsot, A. et. al. (2016, J. Pharm. Pharm Sci 19:411-422). Detection of other analytes, or compounds, in blood, for example but not limited to, albumin, apolipoproteins A1 and B (apoA1 and apoB), total protein, triglycerides, blood sugar, calcium, ionized calcium, phosphate gamma-aminobutyric acid (GABA), alcohol, aldehyde, lactic acid, heamoglobin, blood urea nitrogen (BUN), albumin, apolipoproteins A1 and B (apoA1 and apoB), total protein, triglycerides, bicarbonate, electrolytes, sodium, potassium, magnesium, calcium, ionized calcium, glycated hemoglobin (A1C), high density lipoprotein (HDL), total cholesterol, omega-3 fatty acid, are well known in the art. These known tests may be used to determine the reference measurement of the compound or analyte in subjects who were exposed to a control treatment, or a range of THC under controlled conditions. These values may then be used as an independent variable in producing an algorithm for the non-invasive determination of corresponding blood analyte. These compound specific algorithms may therefore be used to ensure a proper estimation of the compound within the blood of the body part using non-invasively analyte determination.

By selecting a set of compounds or analytes that are associated with a physiological condition or state of a subject, and using standard measurement techniques, a biochemical profile describing the relative concentrations of these compounds may be determined that is correlated with the physiological condition. For example, if the physiological condition (state of interest) is THC induced intoxication, then two or more analytes, including for example but not limited to, delta-9-tetrahydrocannabinol (THC), THC glucuronide (THCGlu), 11-nor-9-carboxy-THC (THC-COOH), 11-hydroxy THC (11-OH-THC), THC-COOH/11-OH-THC ratio, 11-nor-9-carboxy-THC glucuronide (THC-COOGlu), cannabidol (CBD), cannbinol (CBN), cannabigerol (CBG), delta-9-tetrahydrocannabivarin (THCV), THCV-carboxylic acid, 11-nor-9-carboxy-delta-tetrahydrocannabivarin (THCV-COOH), albumin, apolipoproteins A1 and B (apoA1 and apoB), total protein, bilirubin, prolactin, triglycerides, creatinine, cortisol, glucose, lactate, Total 4, uric acid, blood urea nitrogen (BUN), blood sugar, calcium, ionized calcium, magnesium, sodium, phosphate, and GABA may be determined and the relative amounts of these analytes correlated with the physiological condition of THC-intoxication. As a result, these analytes may be used to obtain a biochemical profile which is an indicator of the physiological condition. By using the methods described herein, whole-blood cannabinoid pharmacokinetics that involves a plurality of analytes directly or indirectly derived from THC metabolism, may be considered in determining the status of the physiological condition (physiological state of being).

By biochemical profile it is meant an output that is derived from a set of values obtained from a set of measured analytes that corresponds to a physiological state of interest.

Additionally, the biochemical profile associated with a target state of being, for example a physiological state of interest, may include a plurality of ghost analytes that are observed to change in response to the state of being (or physiological condition), but whose identity may, or may not, be known. Ghost analytes may be characterized by comparing the absorbance spectra across a range of wavelengths under control or background conditions to obtain baseline values for each of the ghost analytes, with the absorbance spectrum obtained across a range of wavelengths in samples obtained under an induced physiological condition or state, and selecting one or more than one ghost analytes that increase or decrease under the induced physiological condition when compared to the baseline ghost analyte values. For example, a ghost analyte may be identified by analyzing the absorbance pattern across a range of wavelengths and identifying the wavelengths that characterize the ghost analyte (i.e. the ghost analyte displays an increase or decreased absorbance at one or more wavelengths that are specific for the ghost analyte). By characterizing the wavelength pattern associated with a ghost analyte, a baseline ghost analyte value for each ghost analyte may be determined and this value compared with each ghost analyte value determined in response to a physiological condition or state. Ghost analytes may include a plurality of analytes that can be used, along with other known analytes, to obtain a fingerprint or biochemical profile that may be used to define the status of a physiological condition as described herein.

This process for identifying and characterizing ghost analytes, or known analytes, may be repeated and appropriate software and machine learning applied to the acquired data sets to further optimize the predictive accuracy of the set of analytes used to determine the biochemical profile and the status of physiological condition. Using machine learning, complex models based on large data sets may be analyzed to identify acceptable "local minima" within the data sets and enable deep neural networks to be trained on identifying sets of analytes associated with the status of the physiological condition. Support vector machines (SVMs) and/or convolutional neural networks (CNNs) may be used with cross validation to provide insight into the algorithm's ability to generalize learned data representations. Cross validation involves partitioning the data into an arbitrary number of groups and iteratively using one of the groups for testing and the remaining for training (Mirowski, P. W., et. al., 2008 IEEE Workshop on Machine Learning for Signal Processing, Cancun, 2008, pp. 244-249). Hyperparameter tuning may be used to develop an accurate, and robust final prediction.

In this way, an adaptive machine learning platform may be used to enable multiple machine learning algorithms to be executed for determining a physiological state of interest of a subject. The machine learning platform may include a plurality of machine learning components, each associated with a machine learning algorithm. For example, a machine learning component may be a component that utilizes one or more trained (or otherwise configured) machine learning algorithms that receive empirical data (e.g., data stored in one or more databases, for example including biochemical profile data, physiological parameter data and/or behavioral parameter data as described herein) to determine patterns or predictions that may be features of an underlying mechanism that generated the data and indicative of the physiological state of interest. The machine learning component may be able to utilize observed examples (e.g., from a set of training data) to capture characteristics of interest which may correspond to an unknown underlying probability distribution associated with the physiological state of interest. The adaptive machine learning system may allow a user to update decision-making strategies. Furthermore, the adaptive machine learning system, when operatively linked and communicating with a central CPU, may allow the central CPU to update decision-making strategies that can then be transmitted to the user of the hand held device, comprising one or more processors configured with executable instructions, in real time, or when the database is updated and the updated outputs are uploaded onto the handheld device, comprising one or more processors configured with executable instructions, as described herein.

Figure 5:
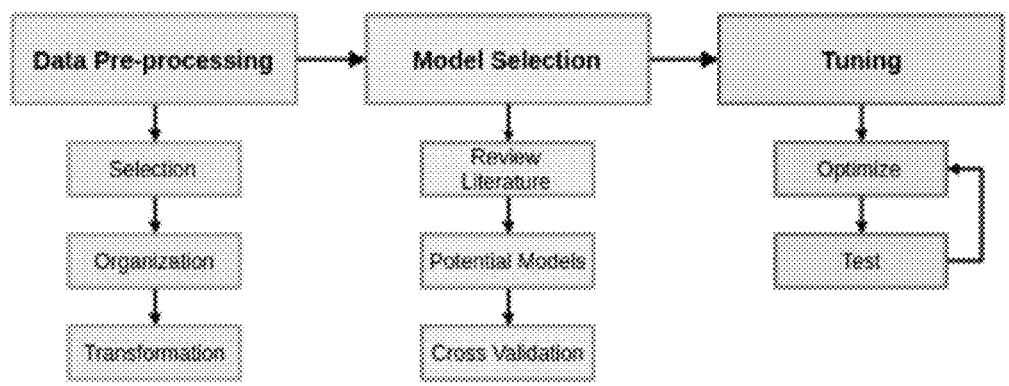
FIG. 5 shows a schematic view of a development pipeline according to an embodiment of the present invention.

The procedure for developing a prediction pipeline, for example, but not limited to a THC prediction pipeline, using machine learning may involve three general steps: data pre-processing, model selection and tuning (see FIG. 5):

Data pre-processing: data pre-processing is used to select high-quality training data from the overall data set, and to organize the data. A microprocessor is directed by software to collect and process the data from the device described herein. The collected data is aggregated, which involves appending new samples to existing database tables, formatted, to ensure that datatypes and column headers are consistent across tables in the database, and cleaned (filtering, interpolating, or keep missing values in the data set as needed), and use by a software model pipeline. Organized data is normalized and engineered features are used to predict intoxication. The features used by the final prediction algorithm may include frequency, time, and spatial domain data including all of the analytes being measured by the spectrometer. As required, engineered features may optionally be extracted using a combination of spatial or frequency domain filtering techniques. Software that may be used for data pre-processing includes, but is not limited to NumPY, SciPy, Pandas, Matlotlib or Seaborn. A microprocessor is directed by software to scan the linear array detector and calculate the second derivative of the spectrum computed. The microprocessor can then calculate the concentration of the particular constituents being measured using the absorbance and second derivative values for a number of selected wavelengths Model Selection: Model architecture is be based on the structure and dimensionality of the data, with known baselines from prior literature on similar datasets being evaluated first before introducing additional complexity. Several algorithms, including but not limited to, support vector machines, deep neural networks, convolution neural networks, and generalized additive models with pairwise interactions may be used in the algorithm development and model selection stage. To ensure that the model complexity (ex. number of nodes, or layers) is appropriately chosen, a bottom up method is used, where an initial logistic regression model acts as a baseline that is compared to each new and increasingly complex model. Machine learning algorithms that may be used to analyze this data include, but are not limited to, support vector machines (SVMs) or convolutional neural networks (CNNs). Machine learning models that are too complex for the problem domain are capable of memorizing individual samples instead of learning the underlying distributions.

Model Evaluation: Cross validation is a data shuffling technique that provides an improved insight into an algorithm's ability to learn an underlying data distribution when limited data is available by testing on a series of training and hold out test splits. For example, data may be split into two subsections (training data and testing data), where the testing data is set aside, and a small percentage of the training data is split again further such that there are several training and testing data sets created from the initial training data subsection. The model is then iteratively trained and validated on these different data sets. The final model is then tested against the original testing data subsection for a final validation. Cross validation makes it easier to observe the generalization ability of the selected model, while also stretching smaller data sets that may otherwise be limited when the data set is split for training (80%) and testing (20%). Software that may be used for model selection includes, but is not limited to NumPY, Pandas, Matlotlib, Seaborn, Tensorflow or Keras.

Tuning stage: the selected model is optimized for performance. For example, hyperparameter search (learning rate, batch size, regularization coefficient, etc.) may be carried out. Hyperparameter tuning is an iterative process that may also be used to develop a robust final prediction. Software that may be used for fine tuning includes, but is not limited to NumPY, Pandas, Tensorflow or Keras.

Continuous Learning: New samples are added to the model using methods including, but not limited to, model weight updating, and champion and challenger. Model weight updating adds another training iteration to the existing model so that the new samples are considered while the model determines the underlying data distribution. Champion and challenger compares the performance of existing models with new models designed on new information with potentially improved insights and or methods. Several continuous learning strategies may be used in tandem.

Therefore, a system is also described herein. The system comprises a computer system that comprises one or more processors programmed with computer program instructions that, when executed, causes the computer system to provide a service platform that enables a developer to obtain training item information for training a machine learning model, for example using the data sets that comprise the biochemical profile, physiological parameters and behavioral parameters as described herein. The training item information indicates inputs and prediction outputs derived from one or more machine learning models' processing of the inputs. Additionally, the computer system may obtain, via the service platform, input/output information derived from one or more machine learning models. The input/output information indicates items provided as input to at least one model of the machine learning models. The service platform may then provide the input/output information derived from the machine learning models to update a first machine learning model, so that the first machine learning model is updated based on the input/output information being provided as input to the first machine learning model. The updated output may then be used to update a device for use within the field, for example, when the device is operatively linked and communicating with a central CPU. In this way, the central CPU (e.g. the service platform) is used update decision-making strategies that are transmitted to the user of the hand held device described herein in real time, or when the database is updated and the updated outputs are uploaded onto the handheld device as described herein.

The biochemical profile may be presented as a ratio of the relative amounts of measured analytes and ghost analytes, or as an index of the measured analytes and ghost analytes. For example, the index may be presented as a proportion of active to inactive analytes, of the various compounds within the blood that are associated, either positively or negatively with the physiological condition.

The above machine leaning process characterizes ghost analytes, known analytes, and other physiological and behavioral parameters, as defined herein, and over time, with repeated data input, the predictive accuracy of the set of analytes, physiological and behavioral parameters is increased.

For example, which is not to be considered limiting, in a THC induced intoxicated state, a subject may comprise the analyte composition presented in Table 1. It is to be understood that this table presents a simplified data set to exemplify the method described herein. Other analytes, which may include known analytes or ghost analytes, are indicated as analytes A, B . . . C; A', B', . . . C'; A", B" . . . C". These other analytes may increase or decrease in response to, or that are correlated with, the physiological condition and they may be included in this analysis. As shown in Table 2, a ratio of the relative abundance of the various selected analytes may be used to obtain a biochemical profile. Alternatively, an index, for example the relative proportion of a group of known "active" analytes (i.e. analytes that are known to be positively correlated with, or produce a THC-intoxicated state, including known and ghost analytes)-to-inactive analytes (i.e. analytes that are known to be correlated with, but not produce the THC-intoxicated state—these analytes may include known and ghost analytes) may be used to derive the biochemical profile.

In the case of smoked marijuana, THC peaks rapidly in the first few minutes after inhaling, and then declines quickly (within hours). THC may then remain at low levels of about 1-2 ng/ml for 8 hours or more. In chronic users, detectable amounts of blood THC can persist for days and therefore this analyte alone is not a reliable indicator of a physiological state of THC-induced intoxication. In chronic users of marijuana, residual THC was detected for 24 to 48 hours or longer at levels of 0.5-3.2 ng/ml in whole blood (1.0-6.4 ng/ml in serum; Skopp G., and Putsch, L., 2004, J. Anal Toxicol. 28: 35-40)

TABLE 2

Analyte composition of a subject before (Control), in an intoxicated state (1 hour after consumption) and post-intoxicated state (36 hours after consumption). THC: delta-9-tetrahydrocannabinol (a bio-active analyte); THC-COOH: 11-nor-9-carboxy-THC (a bio-inactive analyte); 11-OH-THC: 11-hydroxy THC (A bio-active analyte): A (a bio-active analyte), B (a bio-inactive analyte) . . . C (a bio-inactive analyte), A', B', . . . C', A", B" . . . C": analytes that increase, decrease, or that have been correlated with, the physiological condition.

| Analyte State (ng/ml) | THC* | 11-OH-THC | THC-COOH | X | Y . . . | Z | Ratio Active:Inactive |
|---|---|---|---|---|---|---|---|
| 1 hr after consumption | 78 | 5 | 5 | A | B . . . | C | 78:5:5:A:B: . . . :C (17.7 + A)/(B + . . . + C) |
| 36 hr after-consumption | 8 | 2 | 11 | A' | B' . . . | C' | 8:11:2:A':B': . . . C' (1 + A')/(B' + . . . + C') |
| Control | 2 | 0 | 3 | A" | B" . . . | C" | 2:0:3:A":B": . . . C" (0.7 + A")/(B" + . . . + C") |

*THC levels above 3.5-5 ng/ml in blood (or 7-10 ng/ml in serum) indicate likely impairment.

In the example provided in Table 2, in an intoxicated state (1 hr after consumption) the subject exhibits an Active-to-Inactive Index of $(17.7+A)/(B+\ldots+C)$, while the Index associated with a post consumption condition or state, or a control condition or state, are well below this Index $(1+A')/(B'+\ldots+C')$, or $(0.7+A'')/(B''+\ldots+C'')$, respectively. In this example, the result may be considered positive for a THC-induced intoxicated state if the Index is greater than a preset value which is determined based on an analysis of the analytes determined in subjects who were exposed to a control treatment, or a range of THC under controlled conditions, for example an Index value of $(2+A)/(C+\ldots+C)$ may be an indication of a positive result for the state of THC-induced intoxication.

Alternatively, the set of ratios for analyte concentrations determined in subjects who were exposed to a control treatment, or a range of THC under controlled conditions, may be compared against the same set of ratio of analytes for the test subject (as presented in Table 2), and these sets of ratios may be used to determine if a threshold value has been achieved indicating a THC-induced intoxicated state.

Other methods of processing the measured analyte concentration to produce a biochemical profile may be used to determine if a threshold value has been obtained and indicating that the subject is positive for the corresponding physiological state may also be used.

A similar approach as described above may be used to determine the biochemical profile for other physiological states or conditions, for example, but not limited to, alcohol-induced intoxication, a combination of cannabis and alcohol induced-intoxication, or from the consumption of opiates, fentanyl, amphetamines, phencyclidine, sedatives, anxyolytics, cocaine, caffeine, and nicotine.

In addition to obtaining a biochemical profile as an indicator of a physiological condition as descried above, additional physiological parameters may be used to further assist in characterization of the physiological condition or state. Furthermore, behavioral parameters may also be considered in combination with the physiological parameters and biochemical profile data that as acquired. Examples of behavioral parameters include a determination of mental acuity (e.g. the name-face test, fire alarm test, two delayed recall tests, misplaced objects test, shopping list test, digit symbol test), one or more motor skill test (walk and turn test, one leg stand test, horizontal gaze nystagmus test, a divided attention test, a rhomberg balance test), the ability to function at a defined task, for example to operate machinery, drive an automobile, standardized field sobriety.

For example if the physiological condition is cannabis or THC-induced intoxication, then physiological parameters may include, for example but not limited to, heart rate, pulse rate, body temperature, neuropeptide Y, fatty acid amide hydrolase (FAAH), C reactive protein (cRP), creatine kinase (CK), aspartate amino transferase (AAT), alanine transaminase (ALT), gamma-glutamyl transpeptidase (GGT), aspartate aminotransferase (AST), white blood cell count (WBC), red blood cell count (RBC), hemoglobin, hematocrit, neutrophils, lymphocytes, eosinophils, hypoactivity; THC concentration in hair, THC concentration in urine, and this physiological parameter data is combined with the biochemical profile data obtained using two or more than two analytes, for example, but not limited to delta-9-tetrahydrocannabinol (THC), THC glucuronide (THCGlu), 11-nor-9-carboxy-THC (THC-COOH), 11-hydroxy THC (11-OH-THC), THC-COOH/11-OH-THC ratio, 11-nor-9-carboxy-THC glucuronide (THC-COOGlu), cannabidol (CBD), cannbinol (CBN), cannabigerol (CBG), delta-9-tetrahydro-cannabivarin (THCV), THCV-carboxylic acid, 11-nor-9-carboxy-delta-tetrahydrocannabivarin (THCV-COOH), albumin, apolipoproteins A1 and B (apoA1 and apoB), total protein, bilirubin, prolactin, triglycerides, creatinine, cortisol, glucose, lactate, Total 4, uric acid, blood urea nitrogen (BUN), blood sugar, calcium, ionized calcium, magnesium, sodium, phosphate, and gamma-aminobutyric acid (GABA), and any one or more than one ghost analyte that is associated with THC-induced intoxication, in order to produce an output that defines the status of the physiological condition (THC-induced intoxication). Additionally, behavioral parameters, for example determination of mental acuity (for example but not limited to a name-face test, a fire alarm test, a two delayed recall tests, a misplaced objects test, a shopping list test, a digit symbol test), one or more motor skill test (for example but not limited to, a walk and turn test, a one leg stand test, a horizontal gaze nystagmus test, a divided attention test, a rhomberg balance test), the ability to function at a defined task, for example to operate machinery, drive an automobile, standardized field sobriety may be performed and the data combined with the biochemical profile and physiological parameters to determine the physiological condition.

The results from these methods may be combined to produce a value or index of the biochemical profile, the physiological parameter, the behavioral parameter, or a combination thereof, and these values, or index values, may be used to determine if a threshold value has been obtained or exceeded, by comparing the value or index value against a reference value or reference index value, thereby indicating that the subject is positive for the corresponding physiological state.

Similarly, if the physiological state being evaluated is alcohol-induced intoxication, then the physiological parameters may include, but are not limited to, heart rate, body temperature, neuropeptide Y, aspartate amino transferase (AAT), alanine transaminase (ALT), gamma-glutamyl transpeptidase (GGT). This data is combined with the biochemical profile data obtained using two or more than two analytes including, for example but not limited to, alcohol, aldehyde, lactic acid, and any one or more than one ghost analyte that is associated with alcohol-induced intoxication, to produce an output that defines the status of the corresponding physiological condition that is being tested (alcohol-induced intoxication). Additionally, behavioral parameters, for example determination of mental acuity (for example but not limited to a name-face test, a fire alarm test, a two delayed recall tests, a misplaced objects test, a shopping list test, a digit symbol test), one or more motor skill test (for example but not limited to, a walk and turn test, a one leg stand test, a horizontal gaze nystagmus test, a divided attention test, a rhomberg balance test), the ability to function at a defined task, for example to operate machinery, drive an automobile, standardized field sobriety, may be performed and the data combined with the biochemical profile and physiological parameters to determine the physiological condition.

Furthermore, if the intoxicated state being evaluated is, for example resulting from a combination of cannabis and alcohol, or opiates, fentanyl, amphetamines, phencyclidine, sedatives, anxyolytics, cocaine, caffeine, and nicotine consumption, then the physiological parameter may include one or more of: heart rate, pulse rate, body temperature, neuropeptide Y, fatty acid amide hydrolase (FAAH), c reactive protein (cRP), creatine kinase (CK), aspartate amino transferase (AAT), asparate aminotransferase (AST), alanine transaminase (ALT), gamma-glutamyl transpeptidase (GGT), white blood cell count (WBC), red blood cell count (RBC), hemoglobin, hematocrit, neutrophils, lymphocytes, eosinophils, hypoactivity; THC in hair, THC in urine. This data is combined with the biochemical profile data obtained using two or more than two analytes may include: then two or more than two analytes may include: delta-9-tetrahydrocannabinol (THC), THC glucuronide (THCGlu), 11-nor-9-carboxy-THC (THC-COOH), 11-hydroxy THC (11-OH-THC), THC-COOH/11-OH-THC ratio, 11-nor-9-carboxy-THC glucuronide (THC-COOGlu), cannabidol (CBD), cannbinol (CBN), cannabigerol (CBG), delta-9-tetrahydrocannabivarin (THCV), THCV-carboxylic acid, 11-nor-9-carboxy-delta-tetrahydrocannabivarin (THCV-COOH), albumin, apolipoproteins A1 and B (apoA1 and apoB), total protein, bilirubin, prolactin, triglycerides, creatinine, cortisol, glucose, lactate, Total 4, uric acid, blood urea nitrogen (BUN), blood sugar, calcium, ionized calcium, magnesium, sodium, phosphate, GABA, alcohol, aldehyde, lactic acid, and any one or more than one ghost analyte that is associated with alcohol-induced intoxication, to produce an output that defines the status of the corresponding physiological condition that is being tested (a combination of cannabis and alcohol, or opiates, fentanyl, amphetamines, phencyclidine, sedatives, anxyolytics, cocaine, caffeine, and nicotine consumption). Additionally, behavioral parameters, for example determination of mental acuity (a name-face test, a fire alarm test, a two delayed recall tests, a misplaced objects test, a shopping list test, a digit symbol test), one or more motor skill test (a walk and turn test, a one leg stand test, a horizontal gaze nystagmus test, a divided attention test, a rhomberg balance test), the ability to function at a defined task, to operate machinery, drive an automobile, standardized field sobriety (Newmeyer, Swortwood, Taylor, et al., 2017, Clin Chem, 63(3), 647-662. doi:10.1373/clinchem.2016.265371).

The near infrared region of the electromagnetic spectrum may be used for the measurements of samples as described herein. Measurements may be obtained over a range of wavelengths for example from about 400 nm to about 2500 nm range. Chemical species (analytes and ghost analytes) exhibit characteristic absorption bands within this spectral interval which may be used to characterized each analyte. The near infrared region is well-suited to in vivo diagnostic applications since human tissue is transparent to the incident radiation and therefore sufficient penetration of the radiation is possible to allow accurate quantitative analysis.

The source of EMR used in the present invention is preferably near-infrared light, for example but not limited to a polychromatic light source. This type of light source can emit light over a very wide bandwidth including light in the near infrared spectrum. In this case, the light from the light source may pass through a collimator, which is a collection of lenses that concentrate the light into a narrow parallel beam directed at the receptor. The polychromatic light source can be a quartz-halogen or a tungsten-halogen bulb and is powered by a stabilized power source, for example, a DC power supply, or by a battery. This polychromatic light source may be a tungsten-halogen lamp or it may be a collection of LEDs or other light sources selected to emit radiation in the range of about 400-2500 nm, or for example, from about 650 to about 1100 nm.

A receptor is preferably used which is shaped to receive a part of the subject for sampling, for example a clamped part of the skin, or a finger. Alternatively, the receptor could be shaped so that the part of the human, onto which the EMR is to be directed, is placed against the receptor rather than within the receptor. It is preferred that the sampled body part is in close contact with the receptor. Examples of receptors that may be used are provided in US 2013/0248695, U.S. Pat. No. 5,361,758, WO 93/16629, U.S. Pat. Nos. 6,236,047, 6,040,578 or 6,240,306

The EMR is directed onto, and dispersed by, a part of the subject. The dispersed light from the body part, either reflected, transmitted, or both, is collected by using any suitable method, for example, fiber optics, or lenses, and the output signal directed to a diffraction device that separates the wavelengths of light within the output signal into their component parts. Examples of a diffraction device include but are not limited to a diffraction grating or a holographic grating.

The collected signal can comprise EMR that has passed through a part of a subject or has reflected off of a part of the subject, or a combination thereof. The diffracting device may disperses the EMR into its component wavelengths so that the infrared region falls along the length of a detector such as, but not limited to a linear array detector (e.g. a 256 element photo diode array), or a charged couple device (CCD). In the case of an array, the detector has a series of diodes and is preferably electronically scanned by a microprocessor to measure the charge accumulated on each diode, the charge being proportional to the intensity of EMR for each wavelength transmitted through or reflected from the part of the subject in the receptor. The detector is connected to the microprocessor, producing an output spectrum, with the microprocessor analyzing the measurements and ultimately producing a result for each concentration level determined. The result can be stored, shown on a display, or transmitted to another central CPU for further analysis or display. A keyboard may be used to control the device, the central CPU, or both, for example, to specify a particular physiological condition (and corresponding set of analytes) to be measured. The timing and control are activated by the microprocessor to control the device, for example, to determine number and timing of measurements.

After measurements are obtained for the transmittance, reflectance or both, the log of the inverse of these measurements is preferably taken, that is, log FT and log FR, where T and R represent the transmittance and reflectance respectively. A reference set of measurements is taken of the incident light, being the light generated in the device when no part of the subject is in contact with the receptor. The absorbance is then calculated when a part of the subject is in contact with the receptor as a ratio of measurements compared to the reference set of measurements. If desired, a second derivative of the measurements may be obtained to reduce any variation in the result that may be caused by a change in path length for the light caused by measuring the compound concentration in different thicknesses of the parts of the subject. The second derivative calculation may be used to eliminate base line shifts due to different path lengths or absorbing water bands, and in addition, enhances the separation of overlapping absorption peaks of different constituents of the mixture being analyzed. The microprocessor can collect the plurality of spectra produced and calculate the second derivative of the averaged results.

The results obtained may vary with the temperature of the part of the subject, the device used in the method of the present invention may contains a temperature sensor so that the temperature of the analyzed part can be measured rapidly at the time of the spectral sampling. This temperature sensor may comprise a small-mass thermocouple. Computer software can then be used to allow the microprocessor to compensate for spectrum deviations due to the temperature.

The linear array detector is preferably a photo diode array that is positioned to intercept, across its length, the dispersed spectrum from the diffraction grating. The microprocessor is directed by software to scan the linear array detector and calculate the second derivative of the spectrum computed. The microprocessor can then calculate the concentration of the particular constituents being measured using the absorbance and second derivative values for a number of selected wavelengths. A calibration equation is preferably used for each constituent and is determined by the compound being measured.

The measured data may be obtained at the road side, for example by a law enforcement officer, or at a point-of care testing facilities. After the data is collected by the device as described herein, the results may be transmitted to a central computer for further analysis. The measured data may be combined with measured physiological parameters and measured behavioral parameters, and an overall index of the physiological state of interest, for example intoxication, of the subject determined. A plurality of overall indices, each indicative of a physiological state of interest of a subject, may be pooled and delivered for meta-analysis by an interested party, for example health care providers, law enforcement agencies, federal government, or other services that may have an interest in the pooled data.

Also provided herein there is a device for detecting a physiological state of interest of a subject. The device comprises:

a source of electromagnetic radiation (EMR; 30) that emits a plurality of wavelengths of EMR from about 400 nm to about 2500 nm, the source of EMR being operatively coupled to a power source;

a receptor 10 sized to register with, and fit against, a sample 20, the receptor comprising one or more than one port;

one or more than one input radiation guiding element 40 in operable association with the source of EMR, one or more than one output radiation guiding element 50 in operable association with a detector 60, the one or more than one input radiation guiding element and the one or more than one output radiation guiding element in optical alignment with the one or more than one port located and defining an EMR path within the receptor when the receptor is registered with, and fit against, the sample;

the detector for measuring transmitted or reflected EMR received from the sample, the detector operatively coupled to a processing system 70;

the processing system comprising one or more than one algorithm for determining a concentration for two or more than two analytes in the sample, and using the one or more than one algorithm to derive the physiological state of interest of the sample, wherein, the physiological state of interest is:

i) intoxication, then two or more than two analytes may include: delta-9-tetrahydrocannabinol (THC), THC glucuronide (THCGlu), 11-nor-9-carboxy-THC (THC-COOH), 11-hydroxy THC (11-OH-THC), THC-COOH/11-OH-THC ratio, 11-nor-9-carboxy-THC glucuronide (THC-COOGlu), cannabidol (CBD), cannbinol (CBN), cannabigerol (CBG), delta-9-tetrahydrocannabivarin (THCV), THCV-carboxylic acid, 11-nor-9-carboxy-delta-tetrahydrocannabivarin (THCV-COOH), albumin, apolipoproteins A1 and B (apoA1 and apoB), total protein, bilirubin, prolactin, triglycerides, creatinine, cortisol, glucose, lactate, Total 4, uric acid, blood urea nitrogen (BUN), blood sugar, calcium, ionized calcium, magnesium, sodium, phosphate, and gamma-aminobutyric acid (GABA);

ii) alcohol induced intoxication, then two or more than two analytes may include: alcohol, aldehyde, and lactic acid; or iii) intoxication generally, for example arising from cannabis, alcohol, opiates, fentanyl, amphetamines, phencyclidine, sedatives, anxyolytics, cocaine, caffeine, and nicotine consumption, then two or more than two analytes may include: then two or more than two analytes may include: delta-9-tetrahydrocannabinol (THC), THC glucuronide (THCGlu), 11-nor-9-carboxy-THC (THC-COOH), 11-hydroxy THC (11-OH-THC), THC-COOH/11-OH-THC ratio, 11-nor-9-carboxy-THC glucuronide (THC-COOGlu), cannabidol (CBD), cannbinol (CBN), cannabigerol (CBG), delta-9-tetrahydrocannabivarin (THCV), THCV-carboxylic acid, 11-nor-9-carboxy-delta-tetrahydrocannabivarin (THCV-COOH), albumin, apolipoproteins A1 and B (apoA1 and apoB), total protein, bilirubin, prolactin, triglycerides, creatinine, cortisol, glucose, lactate, Total 4, uric acid, blood urea nitrogen (BUN), blood sugar, calcium, ionized calcium, magnesium, sodium, phosphate, GABA, alcohol, aldehyde, and lactic acid.

For example, the device comprising the receptor 10 may be housed in a 'computer mouse-like' housing. To operate the device, an operator activates the program, for example, an App on their cell phone 90 or a program on a remote lap top and turns on the device. The device may comprise an outer layer which is translucent in color and when the device is turned on, the outer layer may turn a yellow hue indicating a standby state. The subject being tested places their body part, for example a finger 20 into a small cavity on the top of the mouse-like receptor 10. Once the finger of the individual is inserted into the cavity and the cavity-body part interface is dark, the light source 30, for example LED's, within the device will be triggered to scan the finger and take a measurement. When the cavity is dark, and the scanning begins the outer layer of the device may change from yellow to green indicating that a sample is being obtained. After a period of time the scanning will be complete, the outer layer of the device may turn red signaling that the test is complete, and the finger can be removed. Data obtained from the test may be processed in the device, or sent to a remote CPU for further processing, for example via blue tooth for further processing.

The updated may then be used to update a device for use within the field, for example, when the device is operatively linked and communicating with a remote or central CPU. In this way, the central CPU may be used update decision-making strategies that are transmitted to the user of the hand held device described herein in real time, or when the database is updated and the updated outputs are uploaded onto the handheld device as described herein.

When used, the device as described above, and based on the biochemical profile, or the biochemical profile in combination with physiological parameter(s), or the biochemical profile in combination with physiological parameter(s) and behavioral parameter(s), may determine that the physiological state of interest of a subject indicative of a state of intoxication has been realized and corrective action may be required. For example, if the device (and optionally physiological parameters and behavioral parameters) is used for road-side testing by a law enforcement officer (a non-limiting example of an operator of the test) and the driver of the car is determined to be in an intoxicated state, then the law enforcement officer may perform corrective action and confiscate the car, suspend the driver's license, press charges and the like.

In other circumstances, the result derived from the device (and optionally physiological parameters and behavioral parameters) may be forwarded to a third party so that corrective action may be taken by the third party. For example, the operator of the test, for example but not limited to, a health care practitioner or the law enforcement officer, may forward the positive result indicating intoxication (impairment) to a third party, for example, a justice of the peace, and corrective action may be taken. Alternatively, if safety is a requirement of the subjects employment, and the subject has been determined to exhibit a positive result indicating intoxication (impairment), then the result may be forwarded to the subject's employer. Examples of situations where safety may be a requirement of the subjects employment, include if the subject is working as an air traffic controller, the subject is a pilot, they operate a commercial vehicle, they operate machinery (large or small) at a work site, they are an operator at a nuclear power facility etc.

To test or calibrate the device a synthetic sample or 'phantom finger' (U.S. Pat. No. 6,657,717, which is incorporated herein by reference) comprised of pre-defined materials may be applied against the receptor. Alternatively, the operator of the device may use their own corresponding body part or finger.

Example: Trial to Assess Physiological State of Interest of a Subject

Participants: approximately 500 patients (3 different people per day, every 5 days a week, every 4 weeks a month, for 8 months). Status of patients regarding usage determined and indexed as heavy users to minimal users. Participants are screened for psychiatric disorders using the Structured Clinical Interview for DSM-IV axis I Disorders (SCID-I). All subjects with a psychiatric disorder warranting treatment are excluded from the study. Females use an approved method of birth control for the duration of the study. Participants refrain from use of cannabis for 72 prior to the text sessions. To determine the participants baseline (pre-test) level of THC, a pre-test saliva and urine sample are obtained and tested for THC. Additionally, a breathalyzer test is performed to detect recent alcohol use.

Demographics: ages 18 to 70, multiple races, multiple skin colors, nationalities, genders, various weights, night time and day time testing, heavy users and novices.

Tests: Participants are asked to eat a light breakfast (e.g. a muffin or bagel) before each test session. Tests are performed on sober patients (background), followed by inducing intoxication and testing from before consumption of the intoxicant to four to six hours after consumption of the intoxicant.

Participants complete subjective effects questionnaires and a baseline driving trial. Once these procedures are complete, participants are given one oral dose of cannabis. Blood, subjective tests, cognitive tests and driving trials, vitals and visual analog scale (VAS) are conducted at regular intervals over 7 hours after dosing.

Intoxication includes a) administering repeated loading of cannabis (as an oil; of from 0 to 75 mg), and b) administering repeated loading of known amount of cannabis (of from 0 to 75 mg), and known amounts of alcohol. Participants drive the driving simulator before and after ingesting oral THC in a single session. Blood is drawn before and during the treatment in order to determine the status of analytes (see below) brought about as a result of a state of impairment. During the test period, each participant reaches an intoxicated state brought about by THC as measured by motor skill and mental acuity impairment.

| | | | Study Session | | | | | | | | | | |
|---|---|---|---|---|---|---|---|---|---|---|---|---|---|
| | Eligibility | Baseline −120 m | Cannabis smoking marks Time 0 | 5 m | 15 m | 30 m | 60 m | 90 m | 2 h | 3 h | 4 h | 5 h | 6 h |
| Driving Trial | X | X | | | | X | | X | | X | | | |
| Breath tests (alcohol.) | X | X | | | | | | | | | | | |
| Infrared detections | | X | | X | X | X | X | X | X | X | X | X | X |
| Physical Exam, Psychiatric Exam (SCID) | X | | | | | | | | | | | | |
| Vital Signs | X | X | | X | X | X | X | X | X | X | X | X | X |
| Urine: Point-of-care drug screen | X | X | | | | | | | | | | | |
| Urine: BSS | X | X | | | | | | | | | | | |
| Urine: Point-of-care pregnancy test | X | X | | | | | | | | | | | |
| Blood: Biochemistry, Hematology | X | | | | | | | | | | | | |
| Blood: THC and metabolites quantification | | X | | X | X | X | X | X | X | | | | |
| Blood: other analytes | | X | | | | X | | X | X | | | | X |
| Saliva: THC detections | X | X | | | | X | | X | X | | | | X [PDC8] |
| VAS | | X | | X | X | X | X | X | X | X | X | X | X |
| Verbal free recall | | X | | | | X | | X | | X | | | |
| Demographics and self-report questionnaire | | X | | | | | | | | | | | |
| Timeline follow back | X | X | | | | | | | | | | | |

Physical Measurements: 1) Breath sample for alcohol; 2) Physical examination 3); Vital signs (temperature, pulse, blood pressure, respiration rate), height and weight; 4) Blood samples to measure biochemistry and haematology, THC, CBD and metabolites quantification (see below); 5)

Urine sample for toxicology screening for drugs of abuse (point-of-care testing); 6) Broad spectrum urine screen; 7) Urine sample for pregnancy testing (point-of-care testing); 8) Saliva sample for determination of saliva THC.

Behavioural Information: 1) Psychiatric examination: Structured Clinical Interview for DSM-IV Axis I Disorders (SCID-I); 2) Timeline Follow Back (TLFB) for 3 months at eligibility assessment and for 7 days at the test session. In the TLFB participants report use of a substance each day for a number days prior to the assessment.

Cognitive/Psychomotor Test: Verbal Free Recall Task for verbal learning and memory.

Subjective Assessment for Cannabis Effects: Self-reports of cannabis effects using Visual Analog Scales (VAS)

The tests are repeated per participant. In addition to a physical examination, the following data is obtained from each participant:

i) a blood draw, and a urine sample, are timed to measure THC in the blood (inhalation of, and/or edible consumption of, cannabis) and analytes, and other physiological parameters are determined, including body temperature, pulse, blood pressure, rate of respiration, C-reactive protein, creatine (IDMS), glucose, blood urea nitrogen (BUN), THC, total protein, albumin, prolactin, potassium, sodium, cortisol, lactate, Total T4, calcium, ionized calcium, uric acid, triglyceride, magnesium, creatine kinase, gamma-glutamyl transferase (GGT), aspartate aminotransferase (AST), total bilirubin, WBC count, RBD count, hemoglobin, hematocrit, neutrophils, lymphocytes, eosinophils.

For patients receiving cannabis, two or more of the following analytes may be determined: delta-9-tetrahydrocannabinol (THC), THC glucuronide (THCGlu), 11-nor-9-carboxy-THC (THC-COOH), 11-hydroxy THC (11-OH-THC), THC-COOH/11-OH-THC ratio, 11-nor-9-carboxy-THC glucuronide (THC-COOGlu), cannabidol (CBD), cannbinol (CBN), cannabigerol (CBG), delta-9-tetrahydrocannabivarin (THCV), THCV-carboxylic acid, 11-nor-9-carboxy-delta-tetrahydrocannabivarin (THCV-COOH), albumin, apolipoproteins A1 and B (apoA1 and apoB), total protein, bilirubin, prolactin, triglycerides, creatinine, cortisol, glucose, lactate, Total 4, uric acid, blood urea nitrogen (BUN), blood sugar, calcium, ionized calcium, magnesium, sodium, phosphate, and GABA. Ghost analytes are also tracked to determine which my correlate with, and can be used to determine, the state of cannabis-induced intoxication. The physiological parameter may include one or more of: heart rate, pulse rate, body temperature, neuropeptide Y, fatty acid amide hydrolase (FAAH), c reactive protein (cRP), creatine kinase (CK), aspartate amino transferase (AAT), asparate aminotransferase (AST), alanine transaminase (ALT), gamma-glutamyl transpeptidase (GGT), white blood cell count (WBC), red blood cell count (RBC), hemoglobin, hematocrit, neutrophils, lymphocytes, eosinophils, hypoactivity; THC in hair, THC in urine.

For patients receiving alcohol in addition to cannabis, additional analytes for testing may include: alcohol, aldehyde and lactic acid. Furthermore, ghost analytes are also tracked to determine which my correlate with, and can be used to determine, the state of cannabis and alcohol-induced intoxication. The physiological parameter may include measurement of: heart rate, body temperature, neuropeptide Y, aspartate amino transferase (AAT), alanine transaminase (ALT), gamma-glutamyl transpeptidase (GGT).

ii) two scans using the non-invasive device described herein, are obtained from the patients finger at the same time as each blood draw (step i) is obtained;

iii) a measure of mental acuity and motor skill function is determined following each cannabis, or cannabis and alcohol loading. The behavioral parameters may include determination of mental acuity (a name-face test, a fire alarm test, a two delayed recall tests, a misplaced objects test, a shopping list test, a digit symbol test), one or more motor skill test (a walk and turn test, a one leg stand test, a horizontal gaze nystagmus test, a divided attention test, a rhomberg balance test), the ability to function at a defined task, to operate machinery (simulated), drive an automobile (simulation, to determine impaired driving skills, including reaction time, collisions, mean speed, mean speed while distracted, lateral control, lateral control while distracted), for each test group (i.e. patients receiving cannabis, or patients receiving both cannabis and alcohol).

Driver Simulator Testing: the simulator consists of a driver's side instrument cluster, steering wheel, controls, and center console as in a GM compact car. The steering wheel, brake and accelerator pedals provide dynamic force feedback. The visual system comprises three 50-inch screens providing a 180° field of view in the front, and two 17-inch side displays providing visual feedback for the left and right blind zones.

Participants receive a series of simulator training trials at the start of the study session to become familiar with the simulated vehicle's steering, accelerator, and braking controls. The driving simulations used for main effects testing consist of a series of driving events designed to assess mechanisms by which cannabis consumption may impact driver performance. Dependent measures of driver performance (e.g., standard deviation of lateral position, mean speed) are based on global performance throughout the entire simulation as well as event-specific performance and are measured using the simulator software. Risk-taking behaviour is assessed by measuring average speed throughout the simulation. A divided attention task is included in some of the driving scenarios to increase cognitive load and to better simulate real-world conditions.

Analysis: Deep neural network (DNN) architecture supplemented by use of generalized additive models (GAMs; which provide the interoperability of logistic regression, with the capability to solve non-linear problems) are used to provide enhanced interpretability of model decisions.

Safety of the patients pre, during and post intoxication is ensured.

All citations are hereby incorporated by reference.

The present invention has been described with regard to one or more embodiments. However, it will be apparent to persons skilled in the art that a number of variations and modifications can be made without departing from the scope of the invention as defined in the claims.

What is claimed is:

1. A method of non-invasively determining a physiological state of interest in a subject comprising,
   (a) placing a body part in contact with a receptor;
   (b) directing a source of electromagnetic radiation (EMR) over a range of wavelengths through the receptor and onto body part so that the EMR reaches the blood and interstitial fluid within the body part;
   (c) measuring the EMR absorbed by, reflected by, or transmitted through, the blood and interstitial fluid of the body part with a detector to obtain a spectrum over the range of wavelengths;

(d) performing a quantitative mathematical analysis of the spectrum using an algorithm to determine an amount of at least one known analyte within the blood and interstitial fluid of the body part, wherein the at least one known analyte is
selected from the group consisting of: delta-9-tetrahydrocannabinol (THC), THC glucuronide (THCGlu), 11-nor-9-carboxy-THC (THC-COOH), 11-hydroxy THC (11-OH-THC), THC-COOH/11-OH-THC ratio, 11-nor-9-carboxy-THC glucuronide (THC-COOGlu), cannabidol (CBD), cannbinol (CBN), cannabigerol (CBG), delta-9-tetrahydrocannabivarin (THCV), THCV-carboxylic acid, 11-nor-9-carboxy-delta—tetrahydrocannabivarin (THCV-COOH), albumin, apolipoproteins A1 and B (apoA1 and apoB), total protein, bilirubin, prolactin, triglycerides, creatinine, cortisol, glucose, lactate, Total 4, uric acid, blood urea nitrogen (BUN), blood sugar, calcium, ionized calcium, magnesium, sodium, phosphate, GABA, alcohol, aldehyde, and lactic acid;
(e) deriving a biochemical profile from the amount of the at least one known analyte and from the spectrum corresponding to multiple ghost analytes whose identities are unknown and that are observed to change in response to the physiological state of interest, wherein the state of interest is impairment or intoxication of the subject; and
(f) analyzing the biochemical profile to determine the physiological state of interest in the subject.

2. The method of claim 1, wherein in the step of directing, the source of EMR is provided over a range of wavelengths from about 400 to about 2500 nm.

3. The method of claim 2, wherein the physiological state of interest in the subject is selected from the group consisting of: intoxication arising from cannabis, alcohol, a combination of cannabis and alcohol, opiates, fentanyl, amphetamines, phencyclidine, sedatives, anxyolytics, cocaine, caffeine, and nicotine consumption.

4. The method of claim 3, wherein the physiological state of interest is:
i) cannabis-induced intoxication, and the at least one known analyte is selected from the group consisting of: delta-9-tetrahydrocannabinol (THC), THC glucuronide (THCGlu), 11-nor-9-carboxy-THC (THC-COOH), 11-hydroxy THC (11-OH-THC), THC-COOH/11-OH— THC ratio, 11-nor-9-carboxy-THC glucuronide (THC-COOGlu), cannabidol (CBD), cannbinol (CBN), cannabigerol (CBG), delta-9-tetrahydrocannabivarin (THCV), THCV-carboxylic acid, 11-nor-9-carboxy-delta—tetrahydrocannabivarin (THCV-COOH), total protein, bilirubin, prolactin, triglycerides, creatinine, cortisol, glucose, lactate, Total 4, uric acid, blood urea nitrogen (BUN), blood sugar, calcium, ionized calcium, magnesium, sodium, phosphate, and GABA;
ii) alcohol-induced intoxication, and the at least one known analyte is selected from the group consisting of: alcohol, aldehyde, lactic acid; or
iii) intoxication arising from cannabis, alcohol, opiates, fentanyl, amphetamines, phencyclidine, sedatives, anxyolytics, cocaine, caffeine, and nicotine consumption, and the at least one known analyte is selected from the group consisting of: delta-9-tetrahydrocannabinol (THC), THC glucuronide (THCGlu), 11-nor-9-carboxy-THC (THC-COOH), 11-hydroxy THC (11-OH-THC), THC-COOH/11-OH-THC ratio, 11-nor-9-carboxy-THC glucuronide (THC-COOGlu), cannabidol (CBD), cannbinol (CBN), cannabigerol (CBG), delta-9-tetrahydrocannabivarin (THCV), THCV-carboxylic acid, 11-nor-9-carboxy-delta—tetrahydrocannabivarin (THCV-COOH), albumin, apolipoproteins A1 and B (apoA1 and apoB), total protein, bilirubin, prolactin, triglycerides, creatinine, cortisol, glucose, lactate, Total 4, uric acid, blood urea nitrogen (BUN), blood sugar, calcium, ionized calcium, magnesium, sodium, phosphate, GABA, alcohol, aldehyde, and lactic acid.

5. The method of claim 1 wherein in the step of analyzing (step f), the physiological state of interest in the subject is determined by processing a plurality of data sets that are representative of the biochemical profile and that have been obtained from a plurality of subjects, cross validating the plurality of data sets, and training at least one deep neural network, support vector machine, convolutional neural network, and generalized additive model, to develop a model comprising at least one algorithm used to identify sets of analytes associated with the status of the physiological state of interest, and the model is used to analyze the biochemical profile of the subject to determine the physiological state of interest in the subject.

6. The method of claim 5, wherein, the model is iteratively trained and validated using different data sets, to produce a validated model, the validated model comprising at least one algorithm used to identify sets of analytes associated with the status of the physiological state of interest, and the model is used to analyze the biochemical profile of the subject to determine the physiological state of interest in the subject.

7. The method of claim 1, wherein the biochemical profile changes over time.

8. The method of claim 1, wherein the biochemical profile is a ratio of relative amounts of the at least one known analyte and the ghost analytes.

9. The method of claim 1, wherein the biochemical profile is an index of biologically active to biologically inactive analytes.

10. A method of non-invasively determining a physiological state of interest of a subject comprising,
(a) determining at least one physiological parameter of the subject;
(b) placing a body part in contact with a receptor;
(c) directing a source of electromagnetic radiation (EMR) over a range of wavelengths through the receptor and onto the body part so that the EMR reaches the blood and interstitial fluid within the body part;
(d) measuring the EMR absorbed by, reflected by, or transmitted through, the blood and interstitial fluid of the body part with a detector to obtain a spectrum over the range of wavelengths;
(e) performing a quantitative mathematical analysis of the spectrum using an algorithm to determine an amount of at least one known analyte within the blood and interstitial fluid of the body part, wherein the at least one known analyte is
selected from the group consisting of: delta-9-tetrahydrocannabinol (THC), THC glucuronide (THCGlu), 11-nor-9-carboxy-THC (THC-COOH), 11-hydroxy THC (11-OH-THC), THC-COOH/11-OH-THC ratio, 11-nor-9-carboxy-THC glucuronide (THC-COOGlu), cannabidol (CBD), cannbinol (CBN), cannabigerol (CBG), delta-9-tetrahydrocannabivarin (THCV), THCV-carboxylic acid, 11-nor-9-carboxy-delta—tetrahydrocannabivarin (THCV-COOH), albumin, apolipoproteins A1 and B (apoA1 and apoB), total protein, bilirubin, prolactin, triglycerides, creatinine, cortisol, glucose, lactate, Total 4, uric acid, blood urea nitrogen (BUN), blood sugar, calcium, ionized calcium, magnesium, sodium, phosphate, GABA, alcohol, aldehyde, and lactic acid;

(f) deriving a biochemical profile from the amount of the at least one known analyte and from the spectrum corresponding to multiple ghost analytes whose identities are unknown and that are observed to change in response to the physiological state of interest, wherein the state of interest is impairment or intoxication of the subject; and (g) analyzing the biochemical profile and the at least one physiological parameter used to determine the physiological state of interest in the subject.

11. The method of claim 10, wherein in the step of directing, the source of EMR is provided over a range of wavelengths from about 400 to about 2500 nm.

12. The method of claim 11, wherein the physiological state of interest of the subject is selected from the group consisting of: intoxication arising from cannabis, alcohol, a combination of cannabis and alcohol, opiates, fentanyl, amphetamines, phencyclidine, sedatives, anxyolytics, cocaine, caffeine, and nicotine consumption.

13. The method of claim 12, wherein the physiological state of interest is:
   i) cannabis induced intoxication, and the at least one known analyze is selected from the group consisting of: delta-9-tetrahydrocannabinol (THC), THC glucuronide (THCGlu), 11-nor-9-carboxy-THC (THC-COOH), 11-hydroxy THC (11-OH-THC), THC-COOH/11-OH-THC ratio, 11-nor-9-carboxy-THC glucuronide (THC-COOGlu), cannabidol (CBD), cannbinol (CBN), cannabigerol (CBG), delta-9-tetrahydrocannabivarin (THCV), THCV-carboxylic acid, 11-nor-9-carboxy-delta—tetrahydrocannabivarin (THCV-COOH), albumin, apolipoproteins A1 and B (apoA1 and apoB), total protein, bilirubin, prolactin, triglycerides, creatinine, cortisol, glucose, lactate, Total 4, uric acid, blood urea nitrogen (BUN), blood sugar, calcium, ionized calcium, magnesium, sodium, phosphate, and GABA, and the physiological parameter is selected from the group consisting of: heart rate, pulse rate, body temperature, neuropeptide Y, fatty acid amide hydrolase (FAAH), c reactive protein (cRP), creatine kinase (CK), aspartate amino transferase (AAT), asparate aminotransferase (AST), alanine transaminase (ALT), gamma-glutamyl transpeptidase (GGT), white blood cell count (WBC), red blood cell count (RBC), hemoglobin, hematocrit, neutrophils, lymphocytes, eosinophils, hypoactivity; THC in hair, THC in urine;
   ii) alcohol-induced intoxication, and the at least one known analyze is selected from the group consisting of: alcohol, aldehyde, lactic acid, and the physiological parameter is selected from the group consisting of: heart rate, pulse rate, body temperature, neuropeptide Y, aspartate amino transferase (AAT), alanine transaminase (ALT), gamma-glutamyl transpeptidase (GGT); or
   iii) intoxication resulting from a combination of cannabis and alcohol, or opiates, fentanyl, amphetamines, phencyclidine, sedatives, anxyolytics, cocaine, caffeine, and nicotine consumption, and the at least one known analyte is selected from the group consisting of: delta-9-tetrahydrocannabinol (THC), THC glucuronide (THCGlu), 11-nor-9-carboxy-THC (THC-COOH), 11-hydroxy THC (11-OH-THC), THC-COOH/11-OH-THC ratio, 11-nor-9-carboxy-THC glucuronide (THC-COOGlu), cannabidol (CBD), cannbinol (CBN), cannabigerol (CBG), delta-9-tetrahydrocannabivarin (THCV), THCV-carboxylic acid, 11-nor-9-carboxy-delta—tetrahydrocannabivarin (THCV-COOH), albumin, apolipoproteins A1 and B (apoA1 and apoB), total protein, bilirubin, prolactin, triglycerides, creatinine, cortisol, glucose, lactate, Total 4, uric acid, blood urea nitrogen (BUN), blood sugar, calcium, ionized calcium, magnesium, sodium, phosphate, GABA, alcohol, aldehyde, and lactic acid, and the physiological parameter is selected from the group consisting of: heart rate, pulse rate, body temperature, neuropeptide Y, fatty acid amide hydrolase (FAAH), c reactive protein (cRP), creatine kinase (CK), aspartate amino transferase (AAT), asparate aminotransferase (AST), alanine transaminase (ALT), gamma-glutamyl transpeptidase (GGT), white blood cell count (WBC), red blood cell count (RBC), hemoglobin, hematocrit, neutrophils, lymphocytes, eosinophils, hypoactivity; THC in hair, THC in urine.

14. The method of claim 10, wherein in the step of analyzing (step g), the biochemical profile and the at least one physiological parameter used to determine the physiological state of interest in the subject are determined by processing a plurality of data sets obtained from a plurality of subjects, each data set derived from the biochemical profile and at least one physiological parameter, cross validating the plurality of data sets, and training at least one deep neural network, support vector machine, convolutional neural network, and generalized additive model, to develop a model comprising at least one algorithm used to identify sets of analytes associated with the status of the physiological state of interest, and the model is used to analyze the biochemical profile and the at least one physiological parameter of the subject to determine the physiological state of interest in the subject.

15. The method of claim 14, wherein, the model is iteratively trained and validated using different data sets, to produce a validated model, the validated model comprising at least one algorithm used to identify sets of analytes associated with the status of the physiological state of interest, and the validated model is used to analyze the biochemical profile and the at least one physiological parameter of the subject to determine the physiological state of interest in the subject.

16. The method of claim 10, wherein the biochemical profile is a ratio of relative amounts of the at least one known analyte and the ghost analytes.

17. The method of claim 10, wherein the biochemical profile is an index of biologically active to biologically inactive analytes.

18. A device for detecting a physiological state of interest of a subject, comprising:
   a source of electromagnetic radiation (EMR) that emits a plurality of wavelengths of EMR from about 400 nm to about 2500 nm, the source of EMR being operatively coupled to a power source;
   a receptor sized to register with, and fit against, a sample, the receptor comprising at least one port;
   at least one input radiation guiding element in operable association with the source of EMR, at least one output radiation guiding element in operable association with a detector,
   the at least one input radiation guiding element and the at least one output radiation guiding element in optical alignment with the at least one port located and defining an EMR path within the receptor when the receptor is registered with, and fit against, the sample;

the detector for measuring transmitted or reflected EMR received from the sample to obtain a spectrum, the detector operatively coupled to a processing system;

the processing system configured to use at least one algorithm for determining a concentration for at least one known analytes in the sample, wherein the processing system is configured to use the at least one algorithm to derive a biochemical profile from the concentration of the at least one known analyte and from the spectrum corresponding to multiple ghost analytes whose identities are unknown and that are observed to change in response to the physiological state of interest, and to analyze the biochemical profile to determine the physiological state of interest of the subject from the sample, wherein, the physiological state of interest is:

i) cannabis induced intoxication, and the at least one known analyte is selected from the group consisting of: delta-9-tetrahydrocannabinol (THC), THC glucuronide (THCGlu), 11-nor-9-carboxy-THC (THC-COOH), 11-hydroxy THC (11-OH-THC), THC-COOH/11-OH-THC ratio, 11-nor-9-carboxy-THC glucuronide (THC-COOGlu), cannabidol (CBD), cannbinol (CBN), cannabigerol (CBG), delta-9-tetrahydrocannabivarin (THCV), THCV-carboxylic acid, 11-nor-9-carboxy-delta—tetrahydrocannabivarin (THCV-COOH), albumin, apolipoproteins A1 and B (apoA1 and apoB), total protein, bilirubin, prolactin, triglycerides, creatinine, cortisol, glucose, lactate, Total 4, uric acid, blood urea nitrogen (BUN), blood sugar, calcium, ionized calcium, magnesium, sodium, phosphate, and GABA;

ii) alcohol induced intoxication, and the at least one known analyte is selected from the group consisting of: alcohol, aldehyde, lactic acid; or iii) intoxication arising from cannabis, alcohol, opiates, fentanyl, amphetamines, phencyclidine, sedatives, anxyolytics, cocaine, caffeine, and nicotine consumption, and the at least one known analyte is selected from the group consisting of: delta-9-tetrahydrocannabinol (THC), THC glucuronide (THCGlu), 11-nor-9-carboxy-THC (THC-COOH), 11-hydroxy THC (11-OH-THC), THC-COOH/11-OH-THC ratio, 11-nor-9-carboxy-THC glucuronide (THC-COOGlu), cannabidol (CBD), cannbinol (CBN), cannabigerol (CBG), delta-9-tetrahydrocannabivarin (THCV), THCV-carboxylic acid, 11-nor-9-carboxy-delta—tetrahydrocannabivarin (THCV-COOH), albumin, apolipoproteins A1 and B (apoA1 and apoB), total protein, bilirubin, prolactin, triglycerides, creatinine, cortisol, glucose, lactate, Total 4, uric acid, blood urea nitrogen (BUN), blood sugar, calcium, ionized calcium, magnesium, sodium, phosphate, GABA, alcohol, aldehyde, and lactic acid.

19. The system of claim 18, wherein the biochemical profile is a ratio of relative amounts of the at least one known analyte and the ghost analytes.

20. The system of claim 18, wherein the biochemical profile is an index of biologically active to biologically inactive analytes.

* * * * *